(12) United States Patent
Kralik

(10) Patent No.: US 7,375,815 B2
(45) Date of Patent: May 20, 2008

(54) OPTICAL DEVICES, SYSTEMS AND METHOD FOR PRODUCING A COLLIMATED LIGHT PATH

(75) Inventor: John C. Kralik, Devon, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 412 days.

(21) Appl. No.: 10/963,865

(22) Filed: Oct. 12, 2004

(65) Prior Publication Data

US 2006/0077390 A1   Apr. 13, 2006

(51) Int. Cl.
*G01N 1/10* (2006.01)
*G01N 21/00* (2006.01)

(52) U.S. Cl. .................................. 356/440; 356/245

(58) Field of Classification Search ................ 356/440, 356/432–436, 246, 244
See application file for complete search history.

(56) References Cited

U.S. PATENT DOCUMENTS

| 4,643,580 | A | * | 2/1987 | Gross et al. ................. 356/440 |
| 5,402,241 | A | * | 3/1995 | Jeannotte et al. ........... 356/436 |
| 5,739,432 | A | * | 4/1998 | Sinha ........................... 73/579 |
| 5,747,349 | A | * | 5/1998 | van den Engh et al. .... 436/172 |
| 5,750,998 | A | * | 5/1998 | Goldman ..................... 250/343 |
| 6,400,395 | B1 | * | 6/2002 | Hoover et al. ................ 348/80 |
| 6,628,382 | B2 | | 9/2003 | Robertson |
| 6,809,826 | B2 | * | 10/2004 | Robertson .................... 356/440 |
| 6,882,425 | B1 | * | 4/2005 | Elsenhans et al. .......... 356/436 |
| 2002/0140931 | A1 | | 10/2002 | Robertson |

* cited by examiner

*Primary Examiner*—Layla G. Lauchman

(57) ABSTRACT

Devices, systems and methods are provided for producing a collimated light path. Theses devices, systems and methods may be used to determine an optical property of a small volume sample.

48 Claims, 17 Drawing Sheets

OPTICAL DEVICES, SYSTEMS AND METHOD FOR PRODUCING A COLLIMATED LIGHT PATH

BACKGROUND OF INVENTION

Liquid samples are often characterized using optical techniques such as photometry, spectrophotometry, fluorometry, or spectrofluorometry. Typically, the liquid is contained in a vessel referred to as a cell or cuvette, two or more of whose sides are of optical quality and permit the passage of those wavelengths needed to characterize the liquid contained therein. When dealing with very small sample volumes (e.g., from about 1 to 2 microliters), it is difficult to create cells or cuvettes small enough to be filled and to permit the industry standard 1 cm optical path to be used. It is also difficult and/or time consuming to clean these cells or cuvettes for use with another sample.

Perspective on the problem of quantifying a 1-2 microliter liquid sample is gained by considering the physical size of such samples. For example, a 1 microliter droplet occupies a cube with 1 mm edge length or a cylindrical volume with height 1 mm and diameter 1.13 mm. In contrast, optical beam dimensions in conventional spectrophotometers are usually much larger. In order to optically quantify samples that have 1-2 microliter volume in a conventional spectrophotometer, the light beam must have a diameter of approximately 1 mm or less.

Absorbance can be measured with path lengths other than 1 cm. The recent advent of small spectrophotometers designed for use with fiber optics has made it possible to consider device geometries not readily possible before.

For example, U.S. Pat. No. 6,628,382, and U.S. Patent Publication 20020140931 disclose an optical instrument in which a narrow beam of light is directed into a microliter sample, by providing light from a broadband light source, via an optical fiber, to a sample stage that consists of a liquid droplet suspended between two multi-mode optical fibers: one source-side fiber and another fiber that guides light to appropriate detection optics, or a "detection-side" fiber. The close proximity between the source-side and detection-side fibers allows enough of the light cone emanating from the source fiber to be collected by the detection-side fiber after passing through a liquid sample.

One drawback with this close coupling approach is that the presence of the fiber ends in the samples can interfere with the insertion of the sample into the sample zone, cleaning of the sample zone, and other access to the sample zone. Another drawback is the inability to change the separation between the ends of the source and detector fibers without significantly altering the amount of light gathered by the detector fiber. Yet another drawback is that the instrument cannot easily be used to measure the transmission of solid samples with thickness greater than a few hundred microns. Further, operation of the instrument depends on the ability to accurately change the height of the sample and therefore the separation between the ends of the source-side and detection-side fibers.

Additionally, in order to allow the introduction of a sample into the sample zone, and to allow access to the sample zone for cleaning and examination, the upper end of the light path is directed through the free end of a pivotable mechanical arm. The light path from the pivot end of the arm to the free end of the arm passes through a rather long, unrestrained, and exposed optical fiber section that loops over from the pivot end of the arm to the free end of the arm, where the end of the fiber must enter the sample vertically in order to properly direct the beam into the sample. This convoluted path increases optical loss (a function of the radius of curvature of bends in the fiber) and imposes constraints on the dimensions of the device, requiring the instrument to have a certain height in order for the optical fiber to approach the sample vertically. Further, the exposed fiber presents the possibility of variable optical transmission as the optical fiber experiences movement as well as risk of breakage. The instrument also may not be easily modified to include additional optical components.

SUMMARY OF THE INVENTION

The invention provides a device for characterizing an optical property (e.g., such a light absorbance) of a liquid sample. In one aspect, the device is a spectrophotometer. However, the design of the device is generally applicable to other optical instruments such as fluorometers, spectrofluorometers, and photometers. In another aspect, the device comprises a sample containment area for receiving a sample container for small volume liquids, e.g., less than about 5 µl, less than about 2 µl, or less than about 1 µl. In one aspect, the sample containment area comprises two substantially parallel surfaces spaced apart by an adjustable distance, wherein sample liquid is confined by the surfaces and the surface tension of the liquid. In a further aspect, the device receives liquids comprising biological molecules, such as nucleic acids (RNA or DNA), polypeptides, or proteins.

In one embodiment, the device provides an optical path that directs a substantially collimated light beam to and from a sample. In one aspect, the device comprises collimation optics that can collimate an optical beam from an output end of a first light path-defining element to provide a substantially collimated beam to an input end of a second light path-defining element in optical communication with a sample containment area. In certain aspects, the optical beam may be collimated to a diameter equal to or less than about 1 mm over a distance L. In one aspect, the distance L corresponds to a distance that is greater or equal to at least one dimension of the sample containment area. In certain aspects, the sample containment area is dimensioned to receive a container such as a sample cuvette. Such a container may be configured to receive small volume samples, such as samples comprising less than about 5 µl, less than about 2 µl or less than about 1 µl. However, in certain aspects, the device may also receive standard-sized microcuvettes, e.g., comprising a 1 cm pathlength.

In certain aspects, the first light path-defining element is a source-side optical fiber and the second light path-defining element is a detection-side optical fiber.

In one aspect, the device comprises an element for diverting the direction of the collimated light beam, thereby directing the substantially collimated beam to a sample in a sample containment area. For example, in certain aspects, the element comprises a right angle beam steering prism that causes a 90-degree diversion of the collimated light beam.

In other aspects, the device also comprises a focusing element for focusing light from a sample to a detector in optical communication with the focusing element. The detector may be used to detect an optical property of the sample, such as light absorbance. In one aspect, the focusing element focuses light into an input end of the second light-determining path.

In one embodiment, one or more optical components of the device may serve as portions of the sample containment area. For example, in certain aspects, a sample containment area is defined by at least two substantially parallel surfaces.

In one aspect, at least a portion of the sample containment area is defined by a light-directing element. In another aspect, at least a portion of the sample containment area is defined by a light-focusing element. However, in a further aspect, neither the output end of the first light-defining element nor the input end of the second light-defining element forms any portion of the sample containment area or otherwise comes into contact with a liquid sample.

The device may contain additional optical elements, including, but not limited to filters or beam shaping optics. For example, such optics may be placed between light diverting elements and a light-focusing element.

The invention additionally provides systems comprising any of the devices discussed above. Such devices for measuring optical properties (absorption, emission, scattering of light) of samples can be compatible with and/or integrated with other devices such as sample handling systems, sample transfer systems, detectors, processors, microprocessors and the like. Additionally, the invention provides computer program products comprising computer readable medium comprising programs or instructions for implementing and/or integrating various system functions.

The invention also provides methods for detecting and/or quantitating an optical property of a sample. In one aspect, the concentration of a component in a sample can be determined by comparing light transmission by a sample without the component to the sample with the component.

BRIEF DESCRIPTION OF THE DRAWINGS

The objects and features of the invention can be better understood with reference to the following detailed description and accompanying drawings. The Figures shown herein are not necessarily drawn to scale, with some components and features being exaggerated for clarity.

DESCRIPTION OF THE INVENTION

Figure 1:
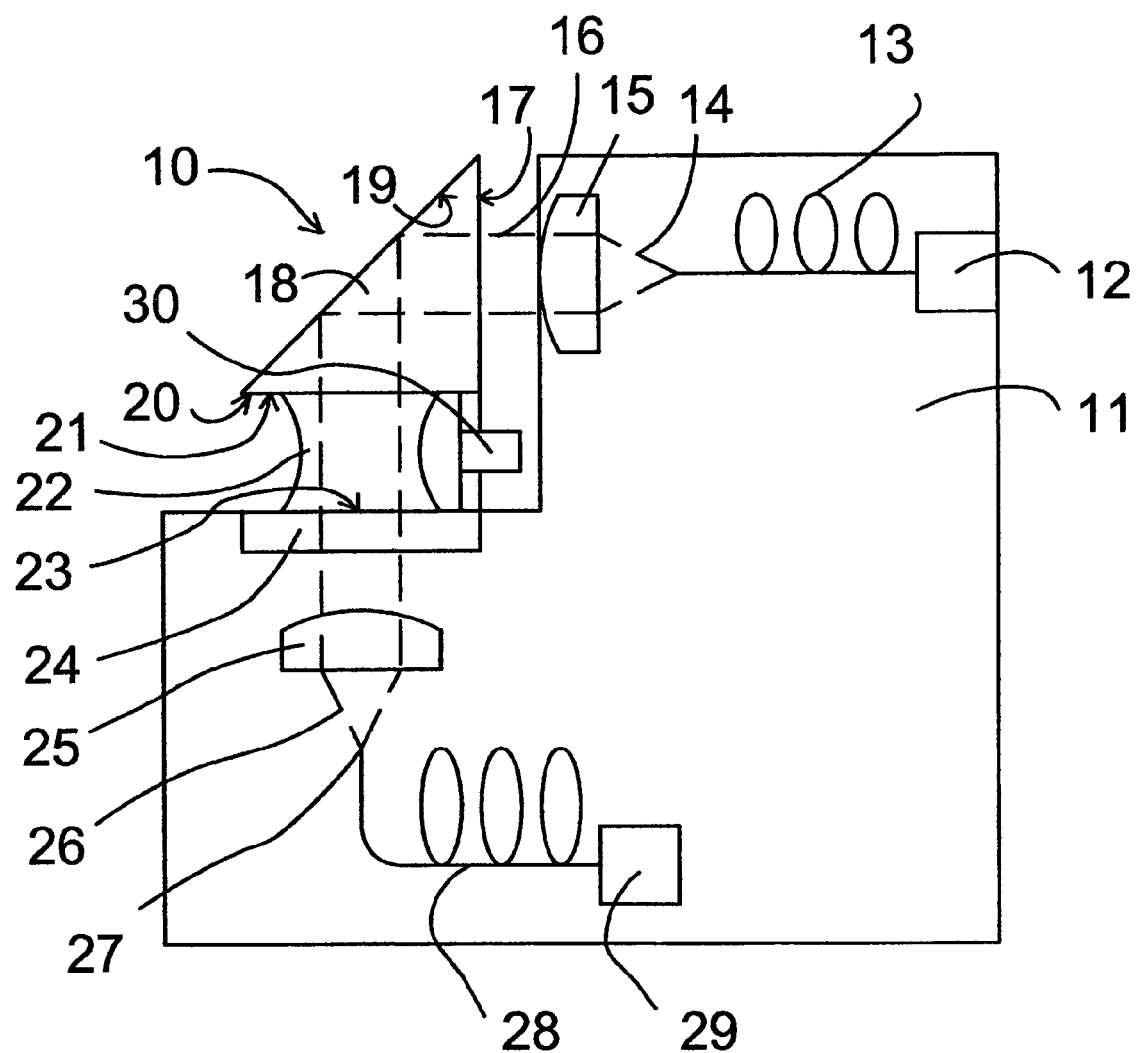
FIG. 1 is a schematic representation of a single prism device according to one aspect of the invention, and showing a light path.

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Unless defined otherwise below, all technical and scientific terms used herein have the same meaning as commonly understood by one of ordinary skill in the art to which this invention belongs. Still, certain elements are defined herein for the sake of clarity.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It must be noted that, as used in this specification and the appended claims, the singular forms "a", "an" and "the" include plural referents unless the context clearly dictates otherwise. Thus, for example, reference to "a biopolymer" includes more than one biopolymer, and the like.

It will also be appreciated that throughout the present application, that words such as "upper", "lower" are used in a relative sense only.

The following definitions are provided for specific terms that are used in the following written description.

A "set" may have one type of member or multiple different types.

A "biopolymer" is a polymer of one or more types of repeating units. Biopolymers are typically found in biological systems and particularly include polysaccharides (such as carbohydrates), peptides (which term is used to include polypeptides and proteins, such as antibodies or antigen-binding proteins), glycans, proteoglycans, lipids, sphingolipids, and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in hydrogen bonding interactions, such as Watson-Crick type, Wobble type and the like. In some cases the backbone of the biopolymer may be branched. Biopolymers may be heterogeneous in backbone composition thereby containing any possible combination of polymer units linked together such as peptide-nucleic acids (which have amino acids linked to nucleic acids and have enhanced stability). As used herein with respect to linked units of a biopolymer, "linked" or "linkage" means two entities are bound to one another by any physicochemical means. Such linkages are well known to those of ordinary skill in the art and include, but are not limited to, amide, ester and thioester linkages. Linkages include synthetic or modified linkages.

Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, PNA, LNA and other polynucleotides as described in U.S. Pat. No. 5,948,902 and references cited therein, regardless of the source.

A "biomonomer" references a single unit, which can be linked with the same or other biomonomers to form a biopolymer (e.g., a single amino acid or nucleotide with two linking groups one or both of which may have removable protecting groups).

The terms "hybridizing", "annealing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides.

"Communicating information" refers to transmitting the data representing that information as signals (e.g., electrical, optical, radio, magnetic, etc) over a suitable communication channel (e.g., a private or public network).

As used herein, a component of a system which is "in communication with" or "communicates with" another component of a system receives input from that component and/or provides an output to that component to implement a system function. A component which is "in communication with" or which "communicates with" another component may be, but is not necessarily, physically connected to the other component. For example, there may be a structural, functional, mechanical, optical, or fluidic relationship between two or more components or elements, or some combination thereof. As such, the fact that one component is said to communicate with a second component is not intended to exclude the possibility that additional components may be present between, and/or operatively associated or engaged with, the first and second components.

"Forwarding" an item refers to any means of getting that item from one location to the next, whether by physically transporting that item or otherwise (where that is possible) and includes, at least in the case of data, physically transporting a medium carrying the data or communicating the data.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture. In certain instances a computer-based system may include one or more wireless devices.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "using" has its conventional meaning, and, as such, means employing, e.g. putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

In one embodiment, the invention provides a device for receiving, containing, and/or moving a liquid sample. In certain aspects, the liquid sample comprises micro-scale volumes, e.g., less than about 5 µl, less than about 2 µl, or less than about 1 µl of sample. In one aspect, the invention provides a device compatible with, or integrated with, a sample analysis system for characterizing (e.g., detecting and/or quantifying) at least one optical property of the sample.

In one aspect, the device comprises a light source and a light path-defining element in optical communication with the light source for defining a light path to and from a sample within a sample containment area. The light source may provide UV and/or visible (VIS) light. Examples of light sources, include but are not limited to, a pulsed Xe lamp, argon lamp, xenon lamp, hydrogen lamp, deuterium lamp, tungsten lamp, arc lamp, hollow cathode lamp, Nernst glower, nichrome wire, globar, lasers, and the like.

An element can comprise an optical fiber coupled to the light source, directly, or indirectly. The optical fiber may comprise a glass fiber coaxially surrounded by a sheath or cladding. In one aspect, the optical fiber is in optical communication with a collimating element for converting diverging light provided by the light source to substantially collimated light.

It should be understood that the term "collimated light" is used to refer to light collimated to a practical degree, that is, "substantially collimated" light. The term "substantially collimated" refers to the degree of collimation that can be practically and economically achieved. As far as the divergence angle of the light that leaves the collimating element, that is, the angle that the outer shell of the beam forms with the axis of the beam, the optimum divergence angle limit is less than 1 degree, the desirable divergence angle limit is less that 3 degrees, and the practical divergence angle limit is less than 5 degrees. In one aspect, the collimating element comprises a refractive element; for example, an achromatic asphere, an achromat, an asphere, a singlet including, but not limited to a ball lens., The device additionally provides an optical path from the collimating element to a light-diverting element comprising a light-diverting surface (e.g., such as a light reflecting surface). The light-diverting element is positioned to divert light along an optical path in optical communication with a sample containment area. In one aspect, the light-diverting surface is movable, e.g., rotatable, tiltable, and/or able to be pivoted about an axis. For example, the light-diverting element may be coupled to a motor such as a servo motor or piezo electric motor which may be controlled by suitable electronic hardware and/or software operatively coupled to the device. In certain aspects, movement of the light-diverting surface is controllable by a processor in communication with the device. Movement routines may be programmed according to time intervals and/or in response to the routing of light through the system. In certain aspects, a user may alter movement routines by providing instructions to the processor to do so, e.g., through a user interface in communication with the processor.

The angle formed by the light-diverting surface and the collimated beam of light may be varied as desired to direct light to a sample containment area within the device. In one aspect, the light-diverting surface comprises a right angle beam-steering prism and collimated light is reflected by total internal reflection on the reflecting surface of the steering prism. The reflected collimated light 16 then passes, at normal incidence, through an output surface of the steering prism. In another aspect, the light-diverting element comprises a mirror, for example, a front-surface, UV-enhanced aluminum mirror.

In certain aspects, light from the light-diverting element is directed to a sample containment area to expose a sample to collimated light. In certain aspects, the sample containment area comprises two substantially parallel surfaces between which a sample may be placed. In one aspect, the light-diverting surface forms one of the substantially parallel surfaces, e.g., such as the upper surface of a containment area defined by substantially parallel upper and lower surfaces.

In another aspect, the device further provides a light path from the sample containment area to an optical detector element. In certain aspects, optical elements for focusing collimated light passing through the sample to be detected by the detector may be provided. For example, in one aspect, the device further comprises a refractive element for substantially converting collimated light to focused light which may be provided via a light path (e.g., such as an optical fiber) to a detector.

Referring first to FIG. 1, which illustrates an aspect of the invention, the various components for defining the light path to a sample and from a sample to a detector are included within a housing or chassis 11 of the device. A fiber-coupled light source 12 (e.g. a pulsed Xe lamp proximity-coupled to multi-mode fiber) is mounted within chassis 11. A source optical fiber 13 transports light 14 from the light source 12 to an achromatic collimating lens 15. The achromatic collimating lens 15 substantially converts diverging light 14 to collimated light 16 and provides collimated light 16, at normal incidence, to an input surface 17 of a right angle beam-steering prism 18. The collimated light 16 is reflected by total internal reflection on the reflecting surface 19 of the steering prism 18. The reflected collimated light 16 then passes, at normal incidence, through the output surface 20 of the steering prism 18.

When a right angle beam-steering prism is used in this way, it causes very little loss and no chromatic dispersion (that is, the reflectance and angle of reflection are not wavelength dependent) of the collimated light that passes through and is diverted 90 degrees by it.

In the embodiment shown in FIG. 1, the output surface 20 of the steering prism 18 forms a first anvil surface 21, which contacts the upper boundary of sample 22. The lower boundary of the sample 22 contacts a second anvil surface 23 on an anvil 24. The separation between the first anvil surface 21 and the second anvil surface 23, which is parallel to it, is variable and may be controlled by spacing controller 30. The collimated light 16 passes through the sample 22 and through the anvil surface 23 and anvil 24 to the achromatic coupling lens 25. The achromatic coupling lens 25 substantially converts the collimated light 16 to focused light 26 and focuses the focused light 26 on the free end 27 of detector optical fiber 28. Detector optical fiber 28 transports the focused light 26 to the light detector optics 29 (e.g. spectrometer or filter wheel with a 1-D or single photo-diode configuration, respectively), where the focused light 26 is detected.

It should be understood that the direction of the light flow can be reversed, by reversing the source and detector, so that the light passes through the sample 22 prior to passing through the prism 18.

Figure 2:
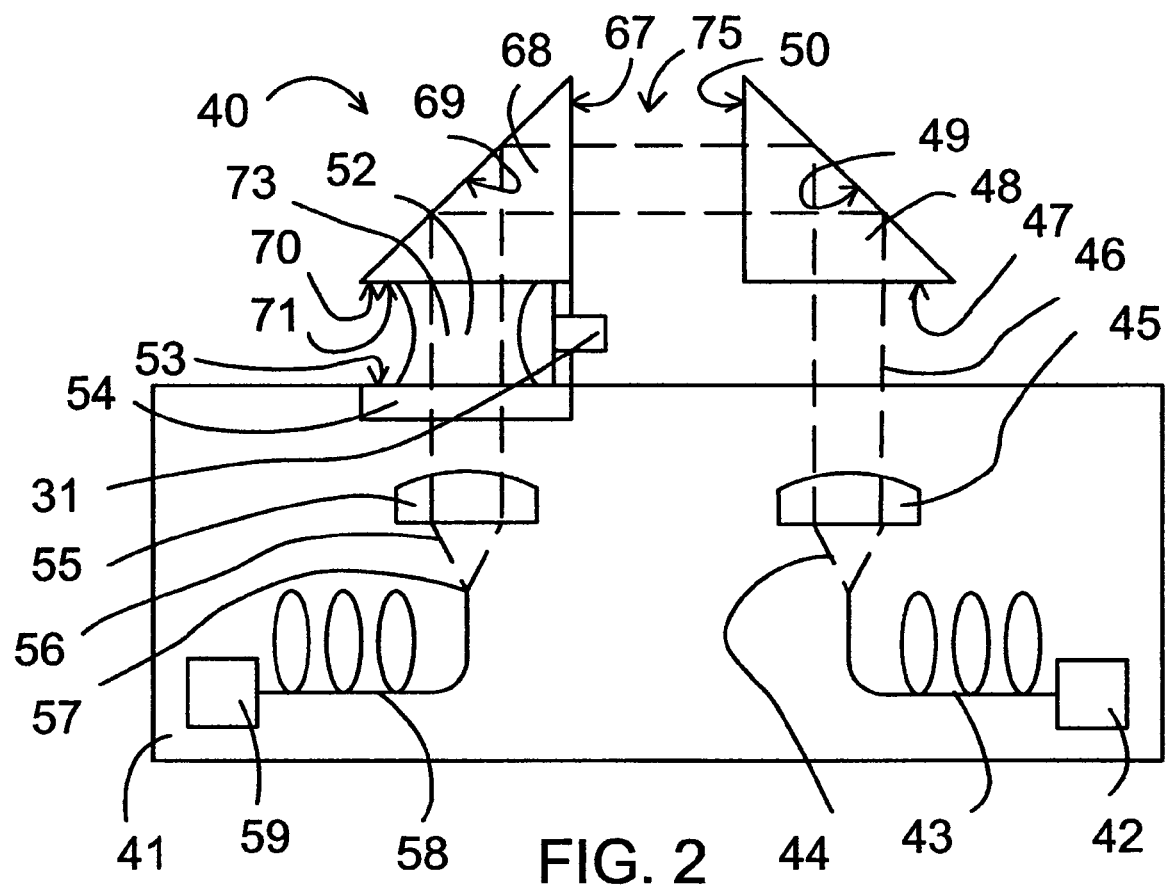
FIG. 2 is a schematic representation of a dual prism device according to one aspect of the invention, and showing a light path.

Referring now to FIG. 2, which illustrates another embodiment of the invention, a device 40, includes a chassis 41. A light source 42 is mounted within chassis 41. A source optical fiber 43 transports light 44 from the light source 42 to an collimating element 45 (e.g., such as an achromatic collimating lens). The collimating element 45 provides substantially collimated light 46 to a light-diverting surface 47 of a light-diverting element 48, shown in FIG. 2 as a right angle beam-steering prism 48. The collimated light 46 may reflected by total internal reflection on the surface 49 of the light-diverting element 48. In one aspect, as shown in the Figure, the reflected collimated light 46 then passes, at 90 degrees, through the output surface 50 of the light-diverting element 48. In this embodiment, one or more additional light-diverting elements are provided. For example, as shown in FIG. 2, the output surface 50 of the light diverting element 48 provides collimated light 46, at normal incidence, to an input surface 67 of a downstream light-diverting element 68, in this case also a right angle beam steering prism.

Figure 7:
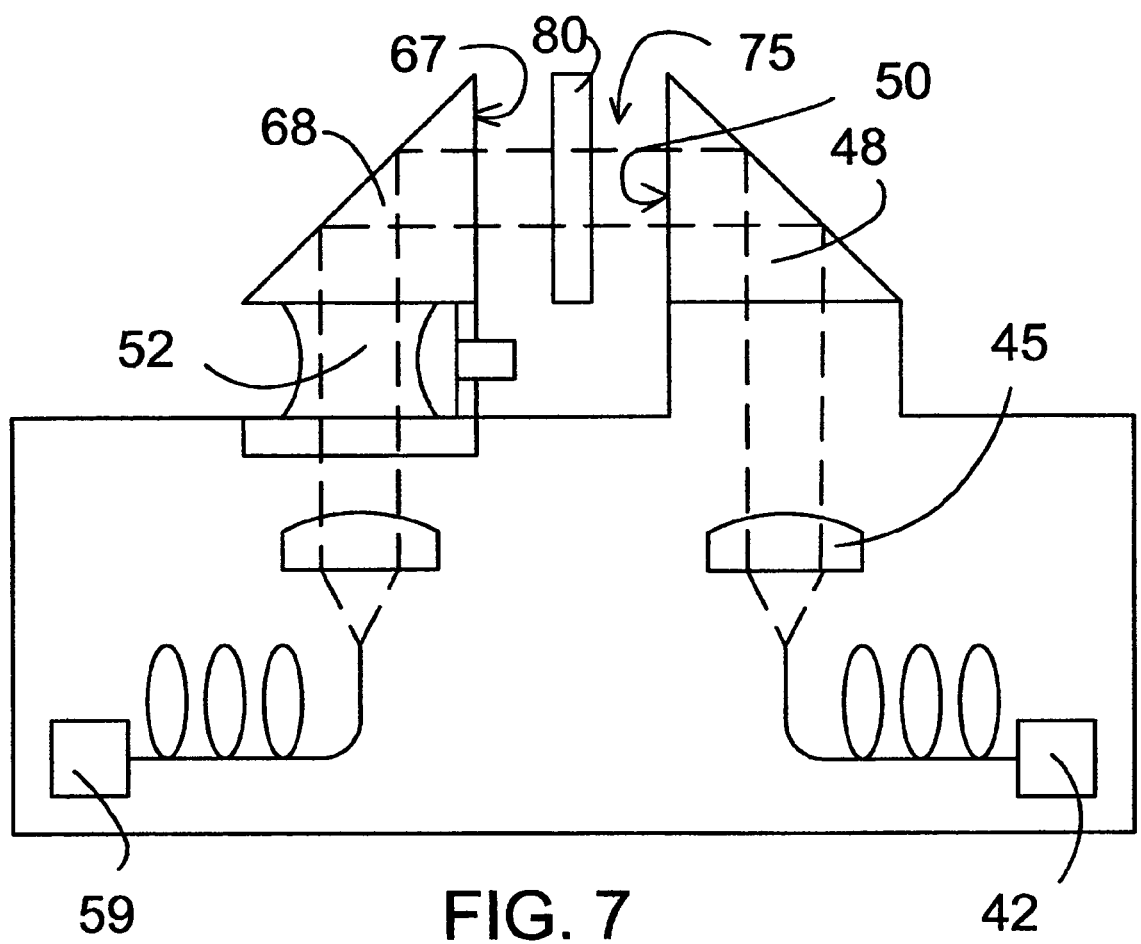
FIG. 7 is a schematic representation of the dual prism device shown in FIG. 2, but with an optically active device in the light path between the prisms.

In one embodiment, the space 75 between the output surface 50 and the input surface 67 is free air and can vary from extremely small to large enough so that filters and other optical elements can be placed in the optical path in the space, as shown in FIG. 7. In one aspect, the light-diverting element forms a Porro prism. A Porro prism is a single prism that functions as would two steering prisms if they were one-piece.

In another aspect, the collimated light 46 is reflected by total internal reflection on the surface 69 of the downstream steering prism 68. The reflected collimated light 46 may then pass, at normal incidence, through the output surface 70 of the steering prism 68. In this embodiment, the output surface 70 of the upstream steering prism 68 forms a first anvil surface 71 which contacts the upper boundary of liquid sample 52. The lower boundary of sample 52 contacts a second anvil surface 53 on anvil 54. Tin one aspect, the collimated light 46 passes through the sample 52 and through the anvil surface 53 and anvil 54 to a focusing lens 55 (e.g., such as an achromatic coupling lens). The lens 55 substantially focuses the collimated light 46, which may be directed to a detector. In one aspect, the focused light as focused light 56, on the free end 57 of detector optical fiber 58. Detector optical fiber 58 transports the focused light 56 to the light detector optics 59, where the focused light 56 is detected.

The separation between the first anvil surface 71 and the second anvil surface 53 may be varied and controlled by spacing controller 31.

It should be understood that the direction of the light flow can be reversed, by reversing the source and detector, so that the light passes through the sample 52 prior to passing through the prism 68.

In one aspect, the spectrophotometer uses two light-diverting elements, one fixed and the other movable. The movable element may be mounted in a protective housing that provides access to the sample zone. In another aspect, the housing is configured to allow access to a surface of a light-diverting element being used as a portion of the sample containment area, e.g., to allow cleaning between measurements. Suitable light-diverting elements, include but are not limited to, steering prisms.

In a further aspect, the device comprises mechanical components for indexing the position of a movable light-diverting element forming a portion of the sample containment area with respect to the second surface forming another portion of the sample containment area and with respect to the fixed light-diverting element. In certain aspects, the device may also include a mechanism to index the height of the movable light-diverting element above the second anvil surface, such as a spacing controller 31. Indexing this parameter may be used to obtain concentration values from the measurement of transmission. Additionally, the height indexing mechanism could be variable to allow the sample thickness to be varied.

Figure 3:
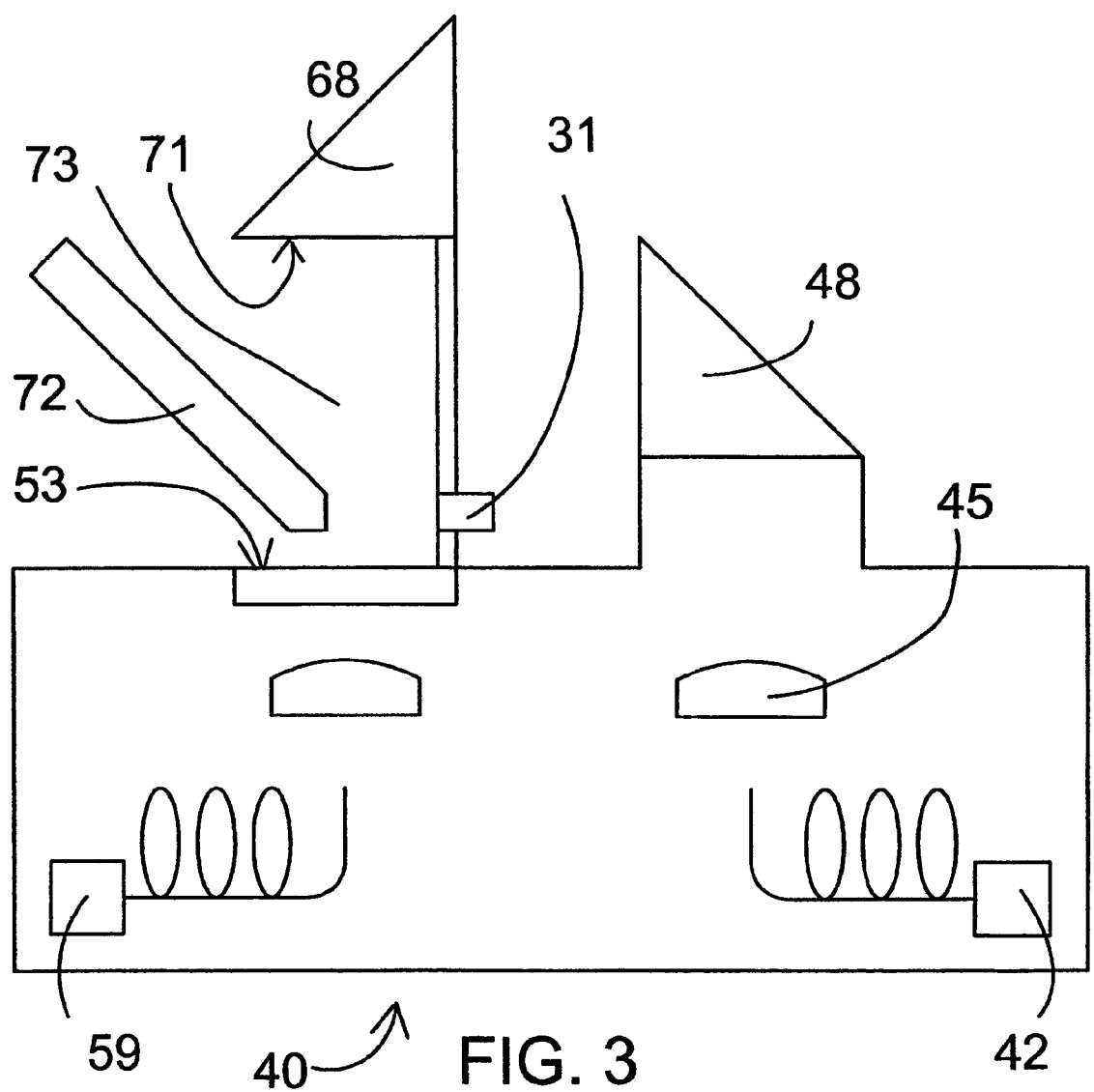
FIG. 3 is a schematic representation of the dual prism device shown in FIG. 2, arranged for the first "no sample" step in its use.

FIG. 3 shows the beginning of the sample loading sequence employed in the embodiment presented in FIG. 2. The downstream steering prism is elevated by spacing controller 31 to provide access to the sample zone 73. In FIG. 3, the light source 42 is turned off, and the end of a pipette 72 is being inserted into the sample zone 73.

Figure 4:
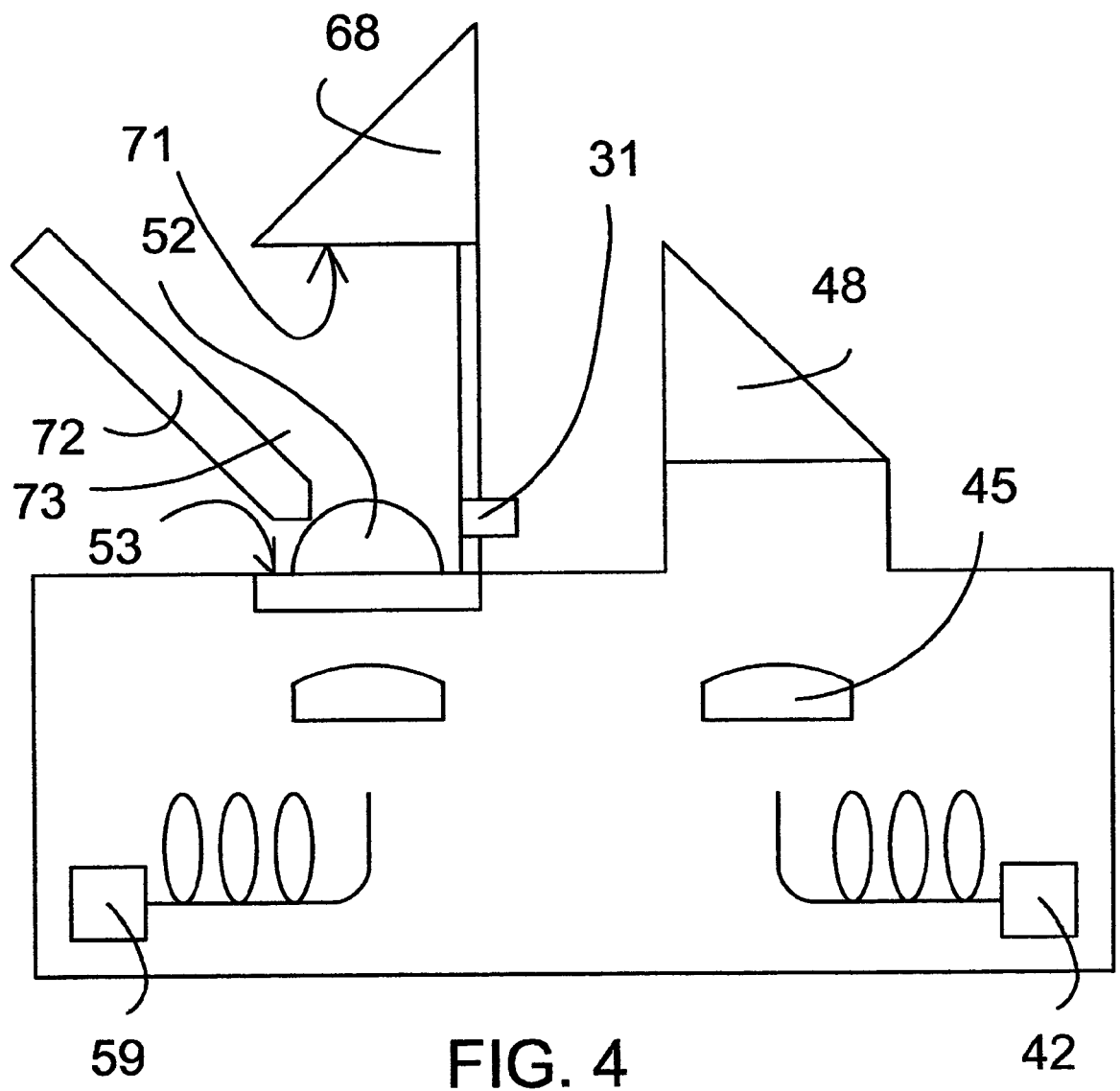
FIG. 4 is a schematic representation of the dual prism device shown in FIG. 2, arranged for the second "droplet" step in its use.

FIG. 4 shows the next step in the process shown in FIG. 3. More specifically, the sample 52, as a droplet, is placed on the second anvil surface 53.

Figure 5:
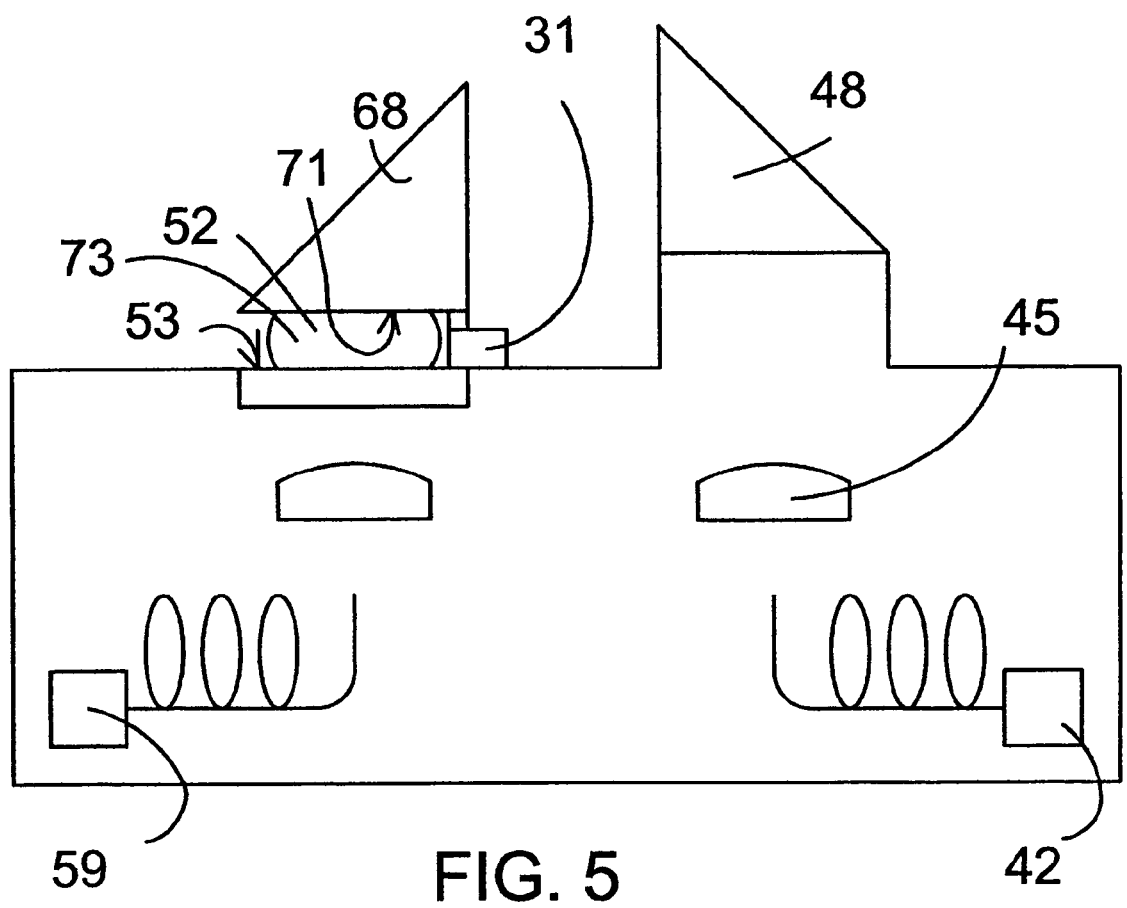
FIG. 5 is a schematic representation of the dual prism device shown in FIG. 2, arranged for the third "sample contact" step in its use.
Figure 6:
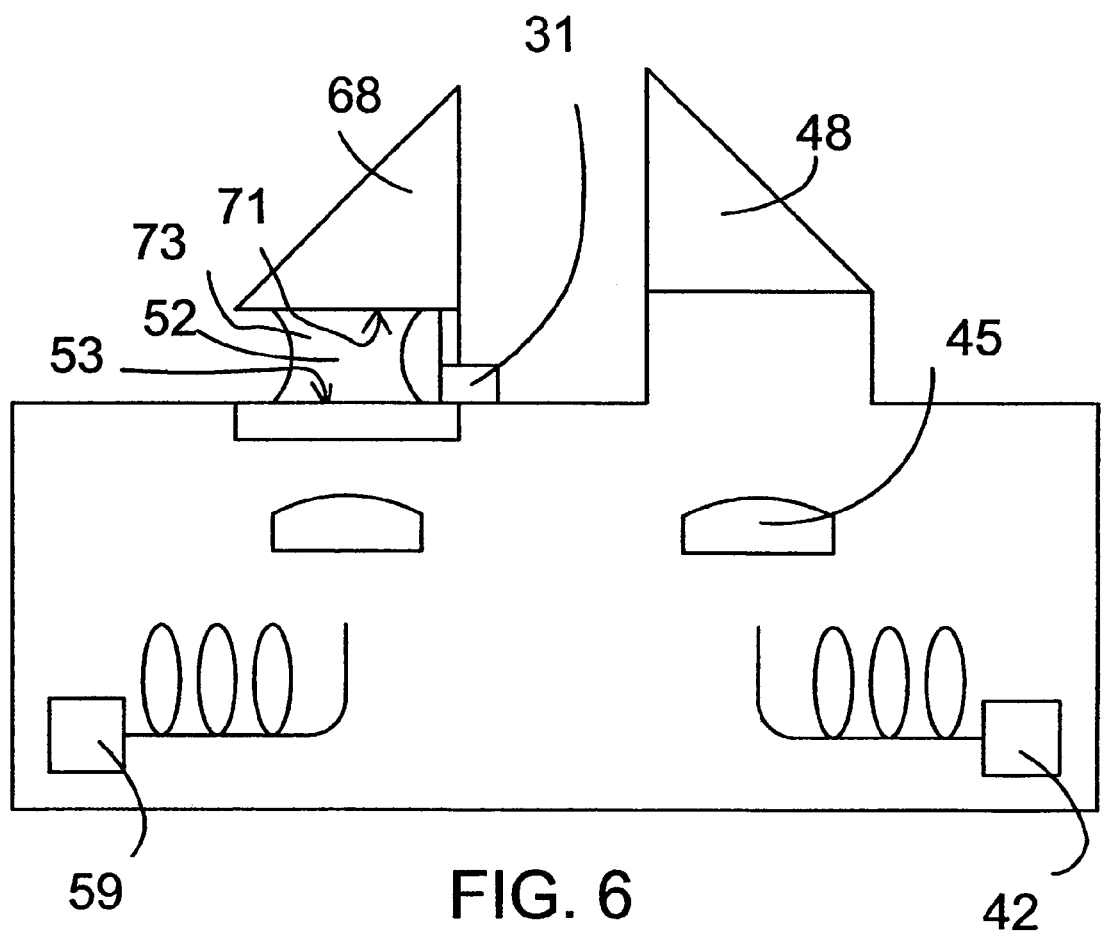
FIG. 6 is a schematic representation of the dual prism device shown in FIG. 2, arranged for the fourth "sample stretch" step in its use.

In FIG. 5, the pipette 72 has been removed and the prism 68 has been lowered so that its anvil surface 71 is contacted by and wetted by the sample 52. In one aspect, the sample 52 is analyzed in this condition. The light source 42 is turned on, as shown in FIG. 2. Because the sample wets the first anvil surface 71 and the second anvil surface 53, the sample can take on a shape as shown in FIG. 2. The spacing controller 31 can be used to measure the distance between the first anvil surface 71 and a second anvil surface 53, which distance is the "length" (L) of the sample 52. An analysis can be done at this sample length. In another aspect, in addition, or alternatively, as shown in FIG. 6, the prism 68 is raised to draw the sample 52 into a column. Surface tension holds the sample onto the first anvil surface 71 and onto the second anvil surface 53, and causes the sample 52 to have slightly concave side-walls. At this point, the light source 42 is turned on, the device and sample takes the configuration shown in FIG. 2, and a measurement can be taken at the resulting sample length.

FIG. 7 shows the device shown in FIG. 2 but shows how a filter or other optical element 80 can be positioned in the space 75 and in the light path between the output surface 50 of the prism 48 and the input surface 67 of the prism 68. This optical element 80 can thereby influence the light going to the sample 52 when the light flow is from prism 48 to prism 68. Conversely, in an alternative arrangement, the optical element 80 can influence the output light when the light flow is going from prism 68 to prism 48.

The optical elements 80 may include notch filters, order-sorting filters, or beam shaping optics. FIG. 7 shows a filter inserted between the two steering prisms that cuts-off IR and/or UV to diminish background light that could corrupt the signal in the form of stray light.

Figure 8:
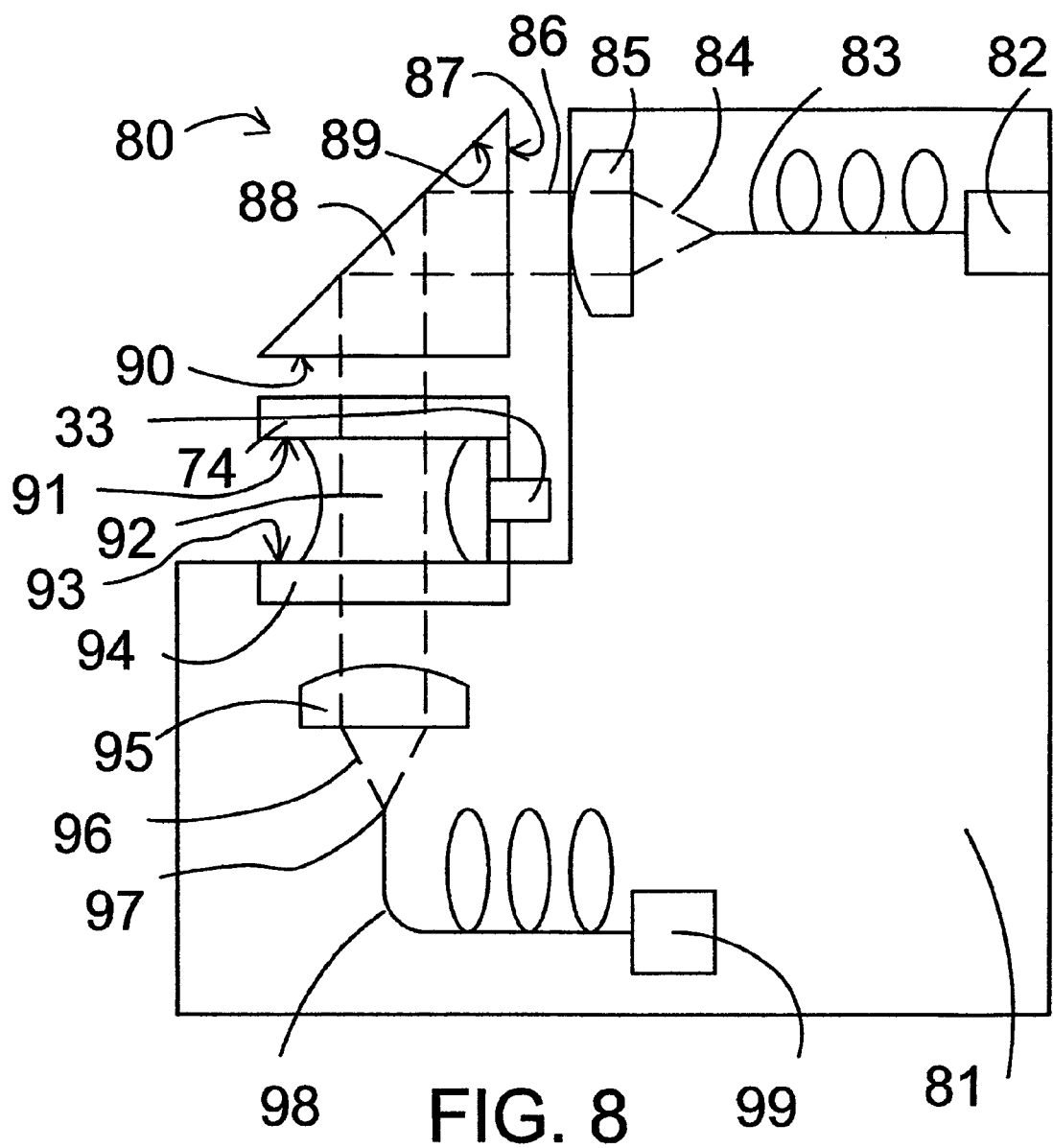
FIG. 8 is a schematic representation of the single prism device similar to that shown in FIG. 1, but with a first anvil separate from the prism.

FIG. 8 shows a variation in the first embodiment shown in FIG. 1, but which can be also employed in the second embodiment shown in FIG. 2. In this variation, the first anvil surface 91, which contacts the upper portion of the sample, is not formed by the output surface 90 of the prism 88, but rather is a surface of a separate anvil 74. The separate anvil 74 is moved by the spacing controller 33 to adjust the spacing between the first anvil surface 91 and the second interval surface 93. In this way, the prism 88 does not have to move while the spacing between the first interval surface 91 and a second anvil surface 93 is varied.

In FIG. 8, as with the embodiment in FIG. 1, device, referred to generally by the numeral 80, includes a chassis 81. A fiber-coupled light source 82 (e.g. a pulsed Xe lamp proximity-coupled to multi-mode fiber) is mounted within chassis 81. A source optical fiber 83 transports light 84 from the light source 82 to an achromatic collimating lens 85. The achromatic collimating lens 85 converts diverging light 84 to substantially collimated light 86 and provides collimated light 86, at normal incidence, to an input surface 87 of a right angle beam-steering prism 88. The substantially collimated light 86 is reflected by total internal reflection on the reflecting surface 89 of the steering prism 88. The reflected substantially collimated light 86 then passes, at normal incidence, through the output surface 90 of the steering prism 88.

In the embodiment shown in FIG. 8, the output surface 90 of the steering prism 88 does not form a first anvil surface 91 which contacts the upper boundary of sample 92. Rather first anvil surface 91 is an undersurface of a separate transparent movable anvil 74. The lower boundary of the sample 92 contacts a second anvil surface 93 on an anvil 94. The substantially collimated light 86 passes through the sample 82 and through the anvil surface 93 and anvil 94 to the achromatic coupling lens 95. The achromatic coupling lens 95 converts the substantially collimated light 86 to focused light 96 and substantially focuses the focused light 96 on the free end 97 of detector optical fiber 98. Detector optical fiber 98 transports the focused light 96 to the light detector optics 99 (e.g. spectrometer or filter wheel with a 1-D or single photo-diode configuration, respectively), where the focused light 96 is detected.

The separation between the first anvil surface 91 and the second anvil surface 93, which is parallel to it, is varied and controlled by spacing controller 33.

It should be understood that the direction of the light flow can be reversed, by reversing the source and detector, so that the light passes through the sample 92 prior to passing through the prism 88.

Figure 9:
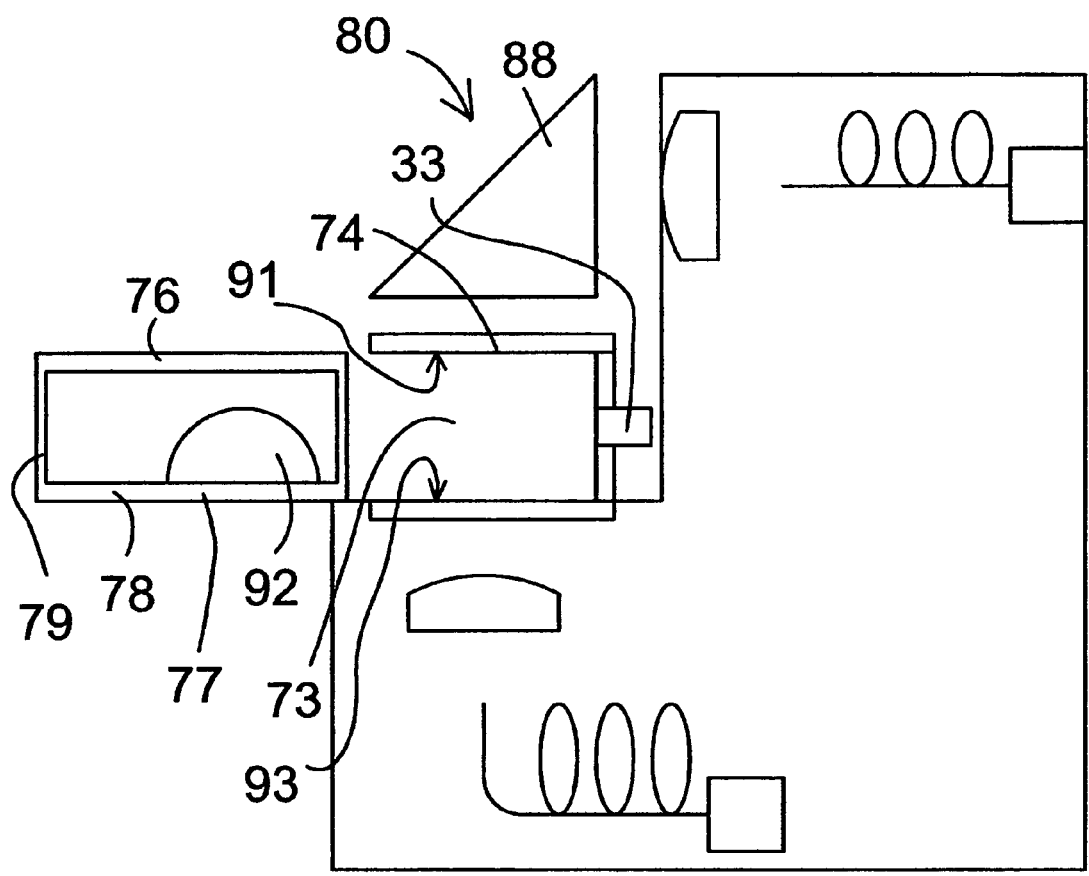
FIG. 9 is a schematic representation of the single prism device shown in FIG. 7, but arranged for use with a separate sample holder.

FIG. 9 shows another way of using the embodiment shown in FIG. 8, which also relates to the FIG. 8 variation in the first embodiment shown in FIG. 1, and which can be also employed in the FIG. 8 variation in the second embodiment shown in FIG. 2. In FIG. 9-12 the light is off. In this variation, as in the variation shown in FIG. 8, the first anvil surface 91 is not formed by the output surface 90 of the prism 88, but rather is a surface of a separate anvil 74. The separate anvil 74 is moved by the spacing controller 33 to adjust the spacing between the first anvil surface 91 and the second anvil surface 93. In this way, the prism 88 does not have to move while the spacing between the first interval surface 91 and a second anvil surface 93 is varied. However in this variation, the first interval surface 91 and the second anvil surface 93 do not actually contact the sample 92 itself but rather contact a transparent roof 76 and floor 77 of a sample holder 78. The sample holder 78 also has flexible walls 79. FIG. 9 shows this variation with the sample holder 78 outside of the sample zone 73, and the sample 92 forming a droplet on the floor 77 of the sample holder 78.

Figure 10:
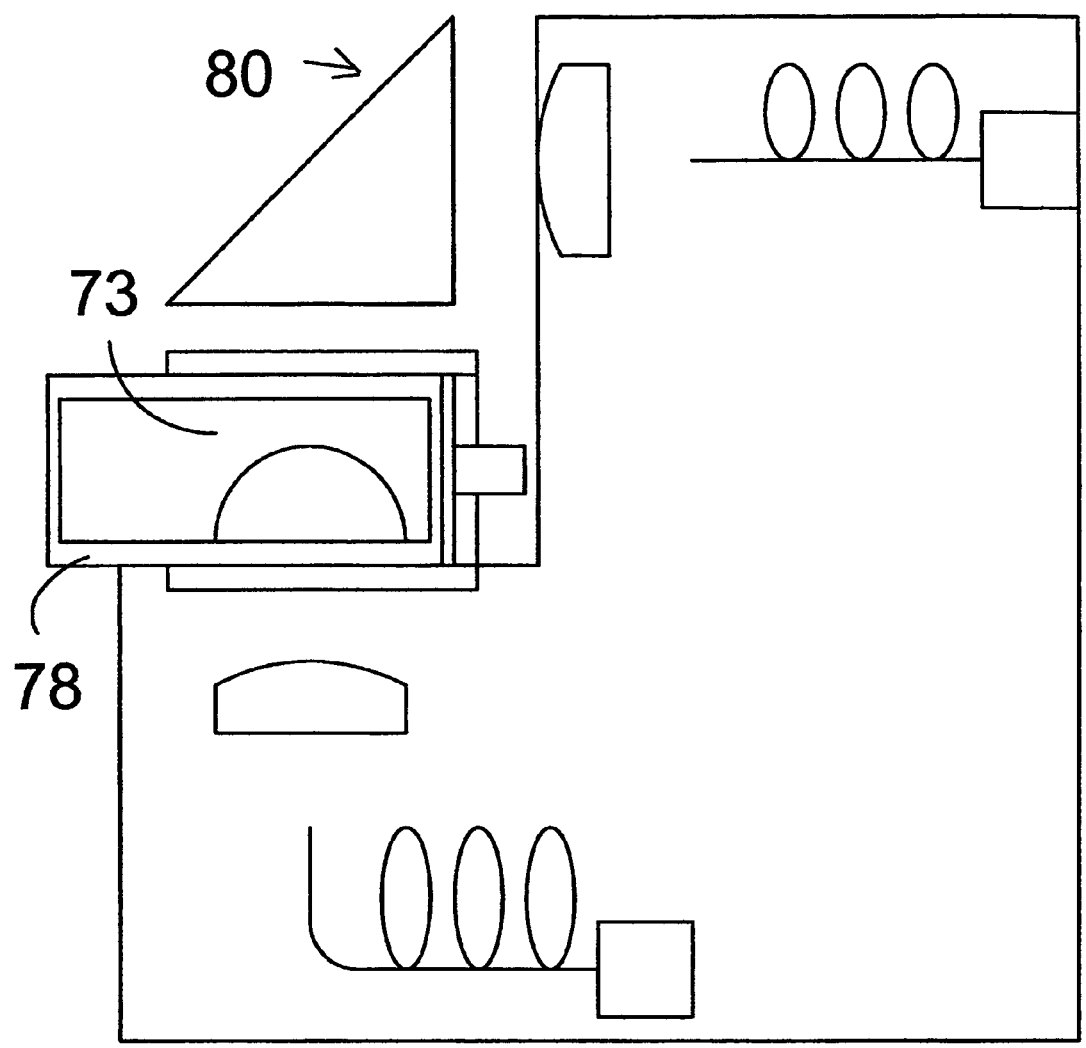
FIG. 10 is a schematic representation of the single prism device shown in FIG. 9, showing the first "insertion" step for use with a separate sample holder.

FIG. 10 shows the variation illustrated in FIG. 9 but with the sample holder 78 inserted into the samples zone 73.

Figure 11:
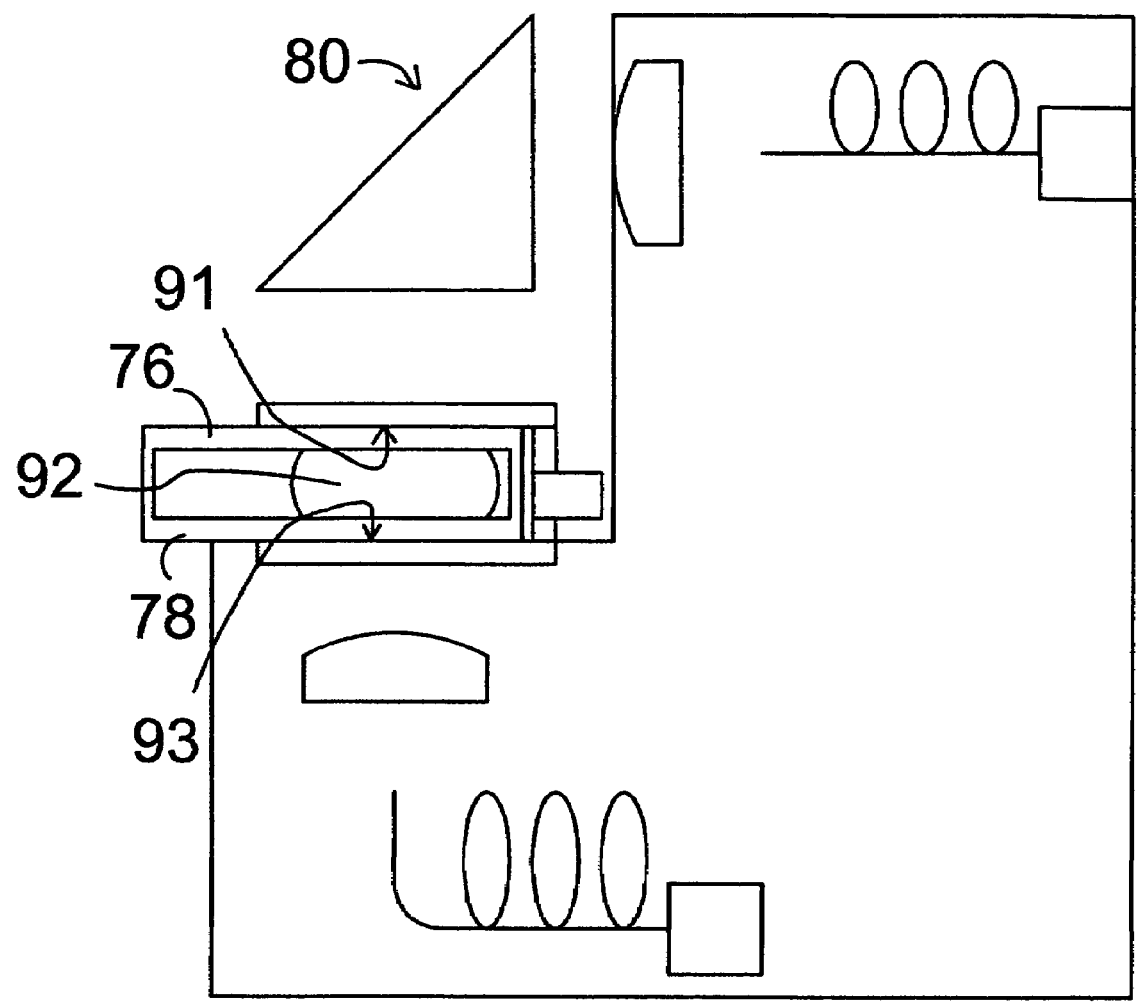
FIG. 11 is a schematic representation of the single prism device shown in FIG. 9, showing the second "sample contact" step for use with a separate sample holder.

FIG. 11 shows the variation illustrated in FIG. 9, but with the sample holder 78 squeezed by first anvil surface 91 and the second anvil surface 93 so that the sample 92 contacts and wets the roof 76 of the sample holder.

Figure 12:
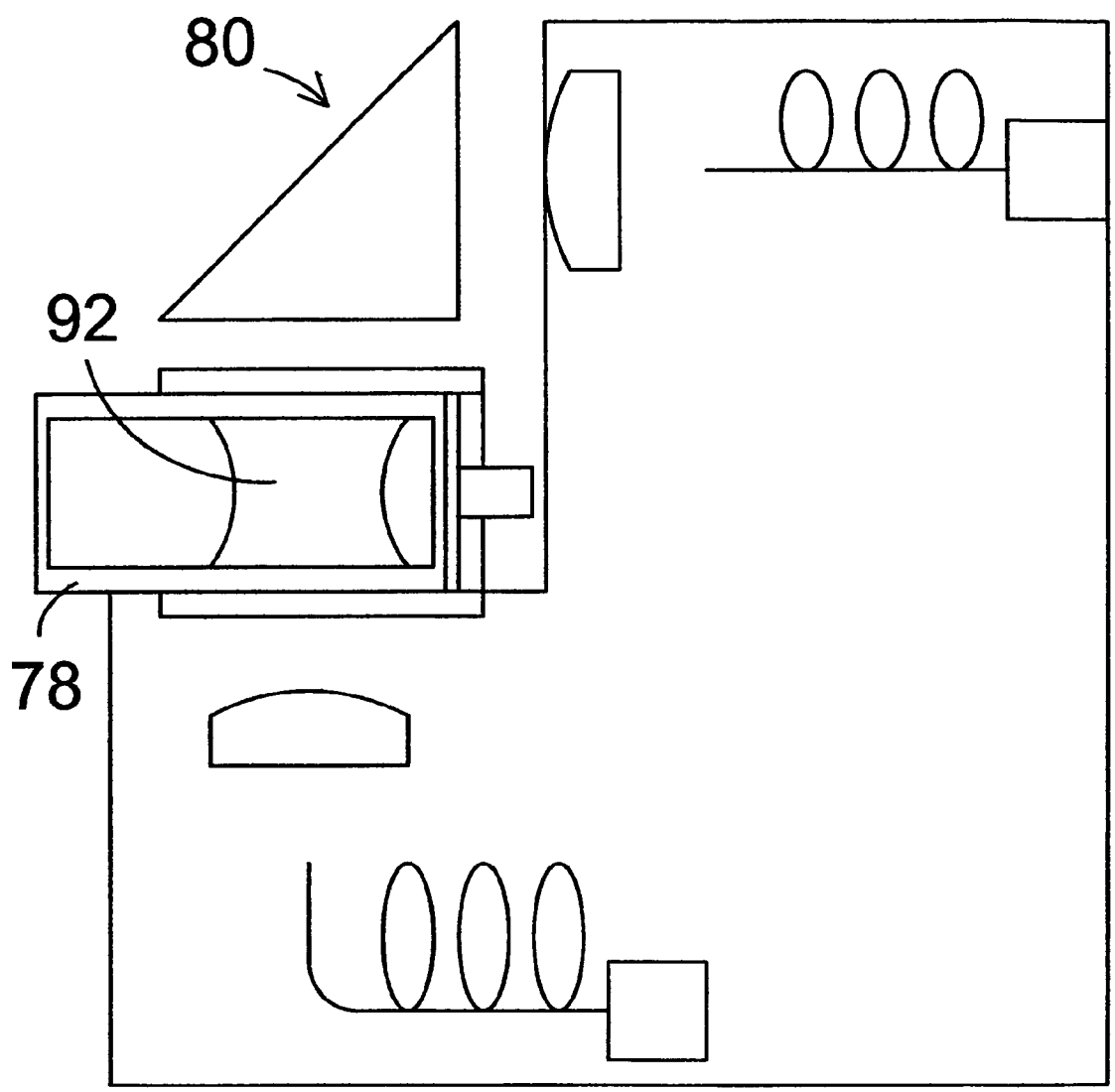
FIG. 12 is a schematic representation of the single prism device shown in FIG. 9, showing the third "sample stretch" step for use with a separate sample holder.

FIG. 12 shows the variation illustrated in FIG. 9, but with the sample holder 78 allowed to expand horizontally to draw the sample 92 into a column.

Figure 13:
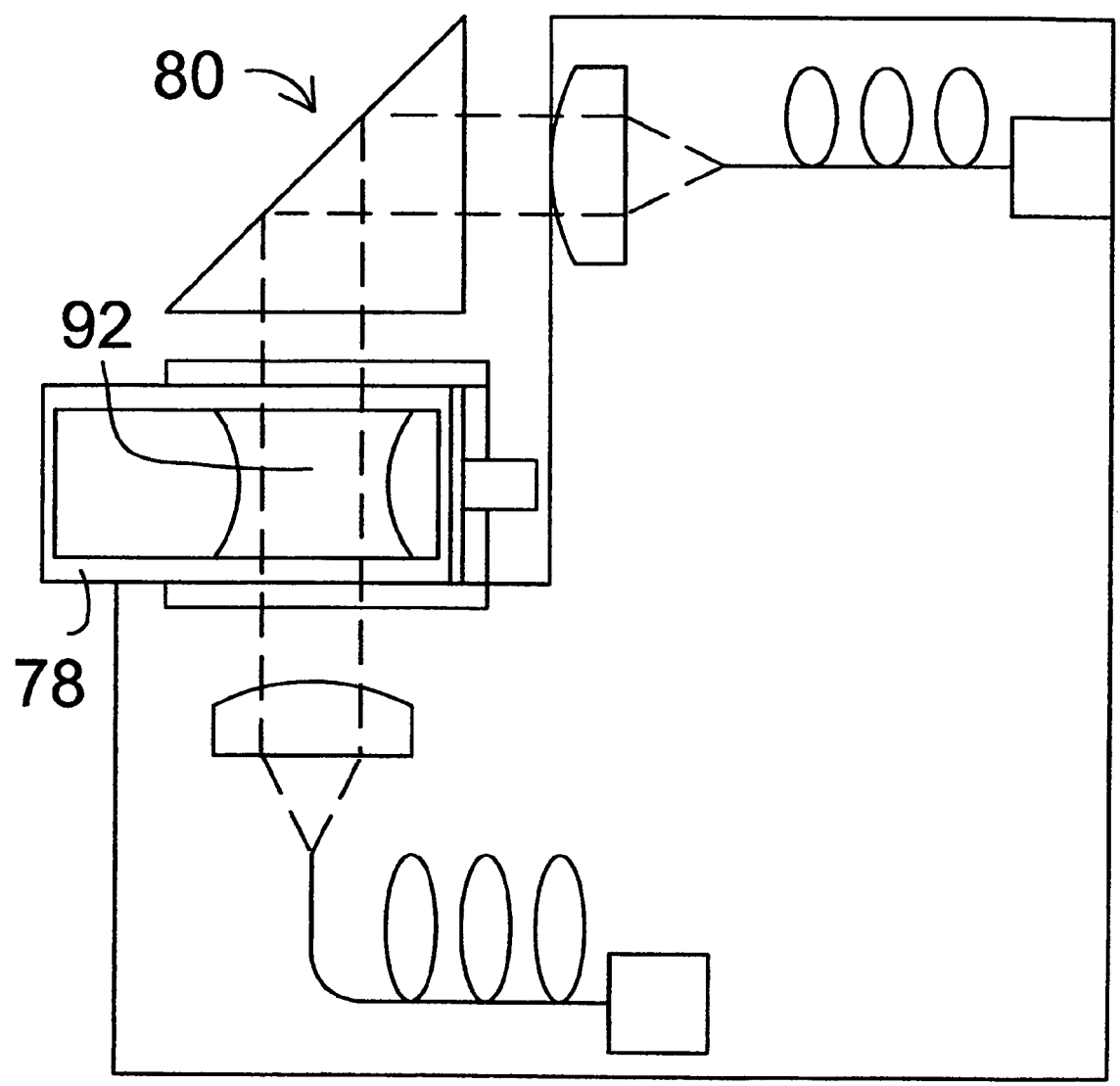
FIG. 13 is a schematic representation of the single prism device shown in FIG. 8, showing the fourth "light on" step for use with a separate sample holder.

FIG. 13 is shows the variation illustrated in FIG. 9, but with the light passing through the sample 92 within the sample holder 78.

The concept of keeping the sample in a separate and optionally sealed or sealable sample holder in a sample containment area provides numerous benefits including the fact that the anvil surfaces do not need to be cleaned after the analysis and the fact that the sample does not contaminate the instrument or the environment nor is the sample contaminated by the instrument or the environment. Furthermore, the sample holder provides a very effective and simplified method for putting the sample into and removing the sample from the sample containment area.

Figure 14:
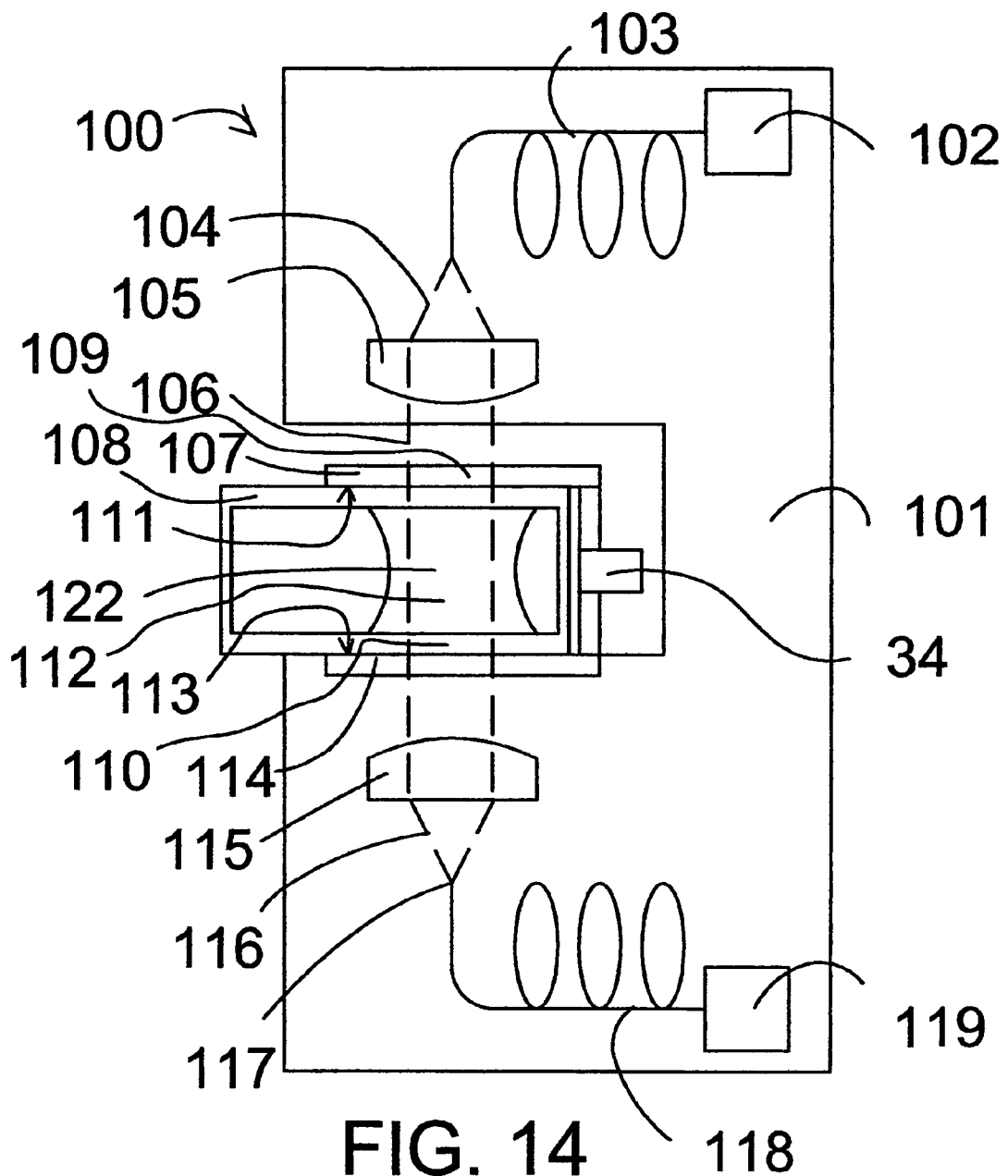
FIG. 14 is a schematic representation of the no prism device embodying the principles of the present invention.

FIG. 14 shows another aspect of the embodiment illustrated in FIG. 13. This aspect eliminates the need for the steering prism. In this aspect, the substantially collimated light 106 is aimed directly into the sample 112. The sample 112 can be placed in the sample zone 122 using the sample holder 108. It is also be possible to insert the sample 112 into the sample zone 122 using conventional technology such as a pipette or capillary.

In FIG. 14, as with the embodiment in FIG. 13, the micro-volume (1-2 microliter sample) spectrophotometer, referred to generally by the numeral 100, includes a chassis 101. A fiber-coupled light source 102 (e.g. a pulsed Xe lamp proximity-coupled to multi-mode fiber) is mounted within chassis 101. A source optical fiber 103 transports light 104 from the light source 102 to an achromatic collimating lens 105. The achromatic collimating lens 105 substantially converts light 104 to collimated light is 106 and provides collimated light 106, at normal incidence, to a first transparent anvil 107. There is no intervening light-diverting element.

In this embodiment, the first anvil surface 111 is an undersurface of the separate transparent movable anvil 107. The collimated light 106 passes through the first anvil 107 and the first anvil surface 111, and then into the sample holder 108.

The upper boundary of the sample 112 contacts the roof 109 of the sample holder 108, and the lower boundary of the sample 112 contacts the floor 110 of the sample holder 108. The collimated light 106 passes through the roof 109 of the sample holder 108, through the sample 112, and through the floor 110 of the sample holder 108, and into the achromatic coupling lens 115. The coupling lens 115 substantially converts the collimated light 106 to focused light 116 and focuses the focused light 116 on the free end 117 of detector optical fiber 118. Detector optical fiber 118 transports the focused light 116 to the light detector optics 119 (e.g. spectrometer or filter wheel with a 1-D or single photo-diode configuration, respectively), where the focused light 116 is detected.

The separation between the first anvil surface 111 and the second anvil surface 113, which is parallel to it, may be varied and controlled by spacing controller 34.

It should be understood that the direction of the light flow can be reversed, by reversing the source and detector, so that the light passes upward through the sample 112.

The embodiment shown in FIG. 14 has the advantage that it needs no steering prism.

Figure 15:
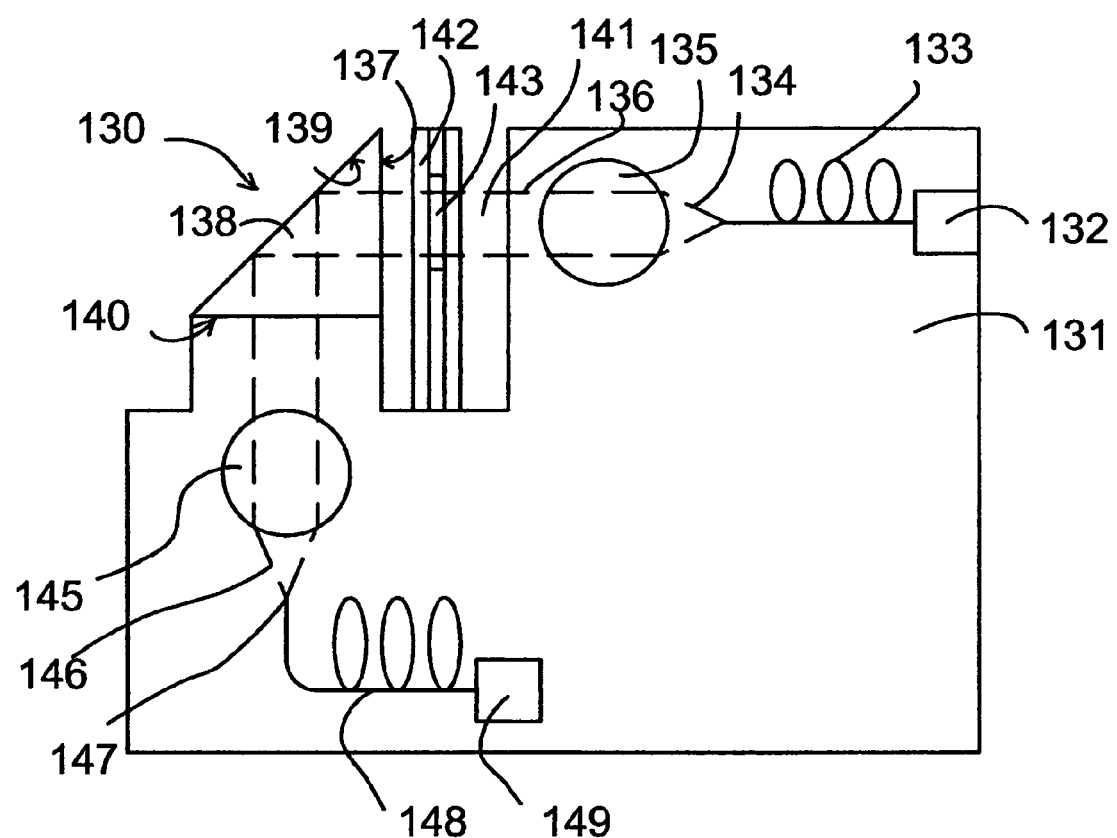
FIG. 15 is a schematic representation of another embodiment of the device of the present invention, employing a single prism and in which the sample is held in a capillary tube.

Referring FIG. 15 which shows the general features of another embodiment of the present invention, the device, referred to generally by the numeral 130, includes a chassis 131. A fiber-coupled light source 132 (e.g. a pulsed Xe lamp proximity-coupled to multi-mode fiber) is mounted within chassis 131. A source optical fiber 133 transports light 134 from the light source 132 to a collimating spherical ball lens 135. The collimating lens 135 converts diverging light 134 to substantially collimated light 136 and provides substantially collimated light 136 to a sample holder 141. In the sample holder 141 is a square-cross-sectioned container 142 positioned with a pair of sides perpendicular to the axis of the collimated light 136. The container 142 is easily moved in and out of the holder 141. The sample 143 is contained in the container 142 and positioned so that the collimated light 136 passes through the sample 143. In one aspect, the container is configured as a capillary.

The substantially collimated light 136 from the sample 142 enters, at normal incidence, an input surface 137 of a right angle beam-steering prism 138, serving as a light-diverting element in this embodiment. The substantially collimated light 136 is reflected by total internal reflection on the reflecting surface 139 of the steering prism 138. The reflected substantially collimated light 136 then passes, at normal incidence, through the output surface 140 of the steering prism 138.

When a right angle beam-steering prism is used in this way, it causes very little loss and no chromatic dispersion of the collimated light that passes through and is diverted 90 degrees by it.

The output surface 140 of the steering prism 138 directs substantially collimated light 136 to a spherical coupling lens 145. The coupling lens 145 converts the substantially collimated light 136 to substantially focused light 146 and focuses the substantially focused light 146 on the free end 147 of detector optical fiber 148. Detector optical fiber 148 transports the substantially focused light 136 to the light detector optics 149 (e.g. spectrometer or filter wheel with a 1-D or single photo-diode configuration, respectively), where the focused light 146 is detected.

It should be understood that the direction of the light flow can be reversed, by reversing the source and detector, so that the light passes through the prism 138 prior to passing through the sample 142.

Figure 16:
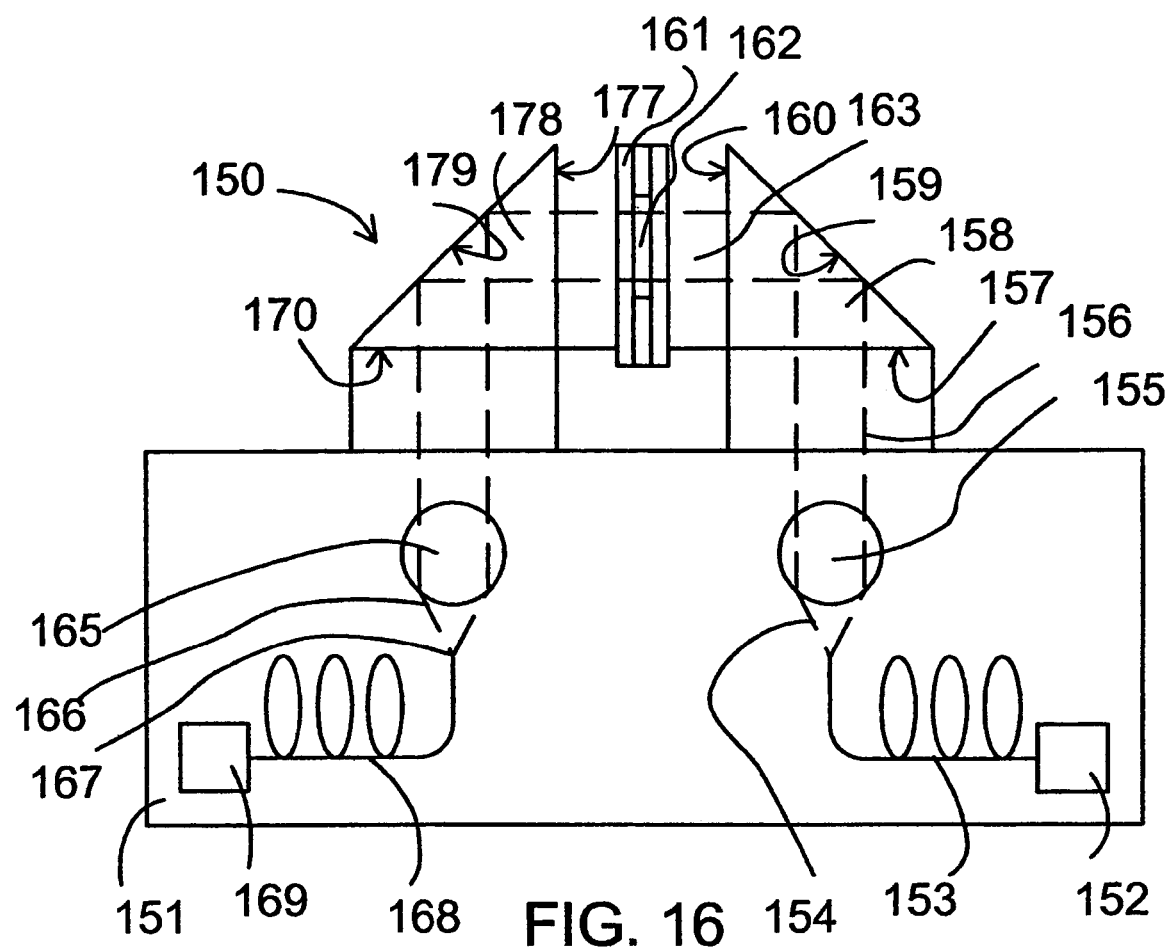
FIG. 16 is a schematic representation of another embodiment of the device of the present invention, employing two prisms and in which the sample is held in a capillary tube.

Referring now to FIG. 16, which shows the general features of another embodiment of the present invention (a dual prism version), the photometer, referred to generally by the numeral 150, includes a chassis 151. A light source 152 is mounted within chassis 151. A source optical fiber 153 transports light 154 from the light source 152 to a spherical collimating lens 155. The collimating lens 155 provides substantially collimated light 156, at normal incidence, to an input surface 157 of an upstream right angle beam-steering prism 158. The substantially collimated light 156 is reflected by total internal reflection on the surface 159 of the upstream steering prism 158. The reflected substantially collimated light 156 then passes, at normal incidence, through the output surface 160 of the steering prism 158.

The substantially collimated light 156 that exits the prism 158 enters a sample capillary holder 163. In the sample capillary holder 163 is a square-cross-sectioned capillary 161 positioned with a pair of sides perpendicular to the axis of the substantially collimated light 156. The capillary 161 is easily moved in and out of the capillary holder 163. The sample 162 is contained in the capillary 161 and positioned so that the substantially collimated light 156 passes through the sample 162.

The substantially collimated light 156 from the sample 162 enters, at normal incidence, an input surface 177 of a right angle beam-steering prism 178. The substantially collimated light 156 is reflected by total internal reflection on the reflecting surface 179 of the steering prism 178. The reflected substantially collimated light 156 then passes, at normal incidence, through the output surface 170 of the steering prism 178.

In this embodiment, the output surface 160 of the upstream steering prism 158 passes substantially collimated light 156. Subsequently, the light passes through the sample capillary holder 163 and the capillary 161 and sample 162 (and any other optical elements in the holder 163 and in the light path), at normal incidence, to an input surface 177 of a downstream right angle beam-steering prism 178.

The capillary holder 163 between the output surface 160 and the input surface 177 is free air and can vary from extremely small to large enough so that, in addition to the capillary 161 and sample 162, filters and other optically active objects can be placed in the optical path in the space of the holder 163. Alternatively, solid samples could be characterized in this embodiment 150 by inserting them into the holder 163 so that the substantially collimated light 156 passes at normal incidence to the input and output planes of said solid sample.

After entering the downstream prism 178, the substantially collimated light 156 is reflected by total internal reflection on the surface 179 of the downstream steering prism 178. The reflected collimated light 156 then passes, at normal incidence, through the output surface 170 of the steering prism 178.

The substantially collimated light 156 passes through the output surface 170 of the steering prism 178 to the spherical coupling lens 165. The coupling lens 165 focuses the substantially collimated light 156, as focused light 166, on the free end 167 of detector optical fiber 168. Detector optical fiber 168 transports the focused light 166 to the light detector optics 169, where the focused light 166 is detected.

It should be understood that the direction of the light flow can be reversed, by exchanging the source and detector, so that the light passes through the sample 162 after passing through the prism 178.

Figure 17:
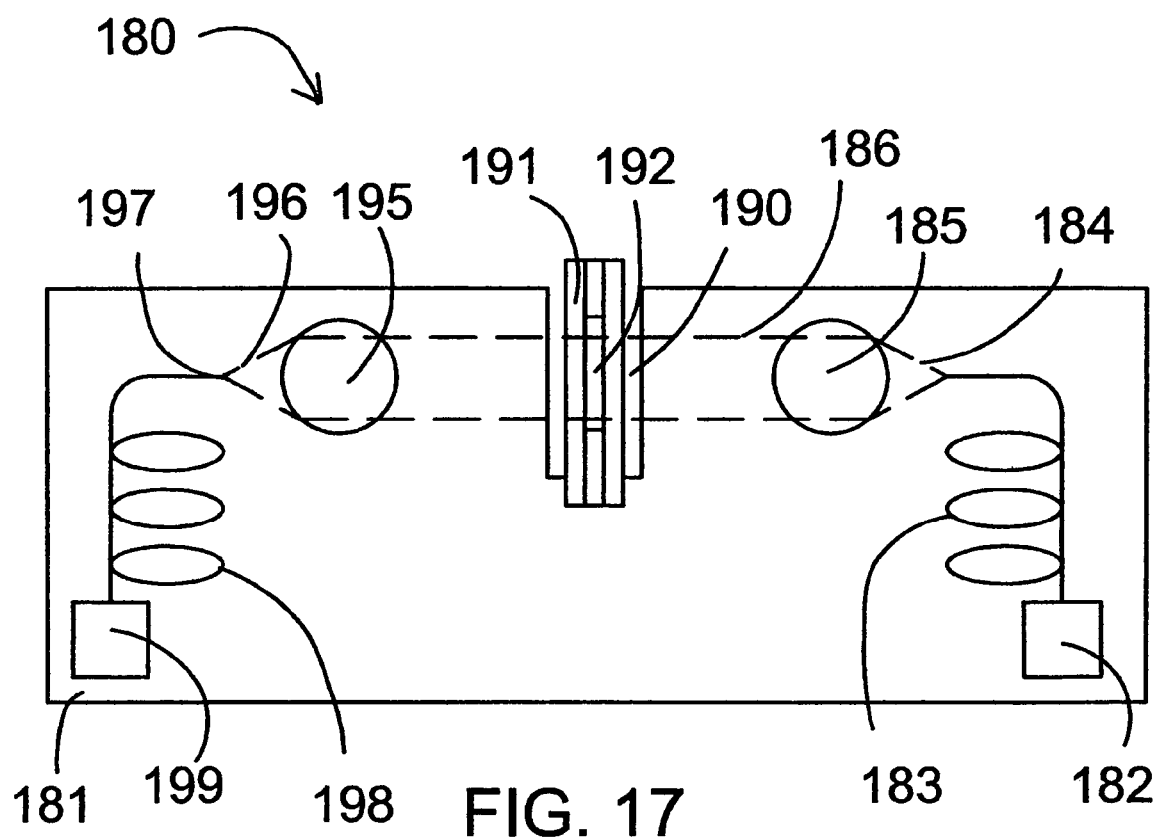
FIG. 17 is a schematic representation of another embodiment of the device of the present invention, employing no prism and in which the sample is held in a capillary tube.

FIG. 17 shows a variation of the embodiment illustrated in FIG. 16. This variation eliminates the need for the steering prisms. In this embodiment, the substantially collimated light 186 is aimed directly into the sample 192. The sample 192 can be placed in the sample capillary holder 190 carried in the capillary 191. This arrangement is only practical because of the long effective length of the collimated light beam 186.

In FIG. 17, as with the embodiment in FIG. 16, device, referred to generally by the numeral 180, includes a chassis 181. A fiber-coupled light source 182 (e.g. a pulsed Xe lamp proximity-coupled to multi-mode fiber) is mounted within chassis 181. A source optical fiber 183 transports light 184 from the light source 182 to a spherical collimating lens 185. The collimating lens 185 converts diverging light 184 to substantially collimated light $i$186 and provides collimated light 186 to a sample holder 190. In the sample holder 190 is a square-cross-sectioned container (e.g., a capillary) 191 positioned with a pair of sides perpendicular to the axis of the substantially collimated light 186. The capillary 191 is easily moved in and out of the capillary holder 190. The sample 192 is contained in the capillary 191 and positioned so that the substantially collimated light 186 passes through the sample 192.

The substantially collimated light 186 passes through sample 192, and into the spherical coupling lens 195. From the collimating lens 185 to the coupling lens 195, there are no intervening steering prisms. The coupling lens 195 converts the substantially collimated light 186 to substantially focused light 196 and focuses the substantially focused light 196 on the free end 197 of detector optical fiber 198. Detector optical fiber 198 transports the substantially focused light 196 to the light detector optics 199 (e.g. spectrometer or filter wheel with a 1-D or single photo-diode configuration, respectively), where the focused light 196 is detected.

It should be understood that the direction of the light flow could be reversed, by exchanging the source and detector, so that the light passes through the sample 192 from left to right.

The embodiment shown in FIG. 17 has the advantage that it needs no steering prisms.

One of the benefits of the present invention is that substantially all of the optical components are built into and supported and protected by the chassis. It is primarily the light beam that is exposed as it passes through the sample zone and sample. This encasement of the optics, and especially the fiber optic cables, allows a more durable and accurate instrument, especially because exposed optical fiber has the disadvantages discussed above.

In addition, a suitable optical information selector is typically used to sort out or discriminate the desired optical signal from the several potentially interfering signals produced by the encoding process. For instance, a wavelength selector can be used to discriminate on the basis of wavelength, or optical frequency. A radiation transducer or photodetector is then activated to convert the optical signal into a corresponding electrical signal suitable for processing by the electronic circuitry normally integrated into the analytical equipment. In one aspect, a readout device provides human-readable numerical data, the values of which are proportional to the processed electrical signals. The data may be provided in a printed form and/or in electronic form. In certain aspects, the data is provided to a remove use, e.g., in the form of an email message or data provided in a webpage.

In another embodiment, the invention provides a method for optically analyzing a small volume liquid. In one aspect, invention provides methods for routing light from a light source to a sample containment site and from the sample containment site to a light receiving device or detector coupled to a processor for receiving information about an optical property of the sample. Light may be routed to and from a sample using any of the devices disclosed above.

Samples can also be measured with a differential absorbance path. Here sample absorbance can be measured by changing the optical path length (sample height) over which the absorbance is measured, measuring the sample at each of one or more path lengths, where the difference in path length combined with the difference in transmitted intensity can be used to calculate the sample absorbance. This can be of significant value if the sample is highly absorbing and the accuracy of the path difference for a small path difference can be better determined than the absolute full optical path. Measurements may be taken with a relatively long path and with a relatively short path length between the moveable anvils carrying the facing surfaces with one or more path differences. If the absorbance at the shorter path is subtracted from the absorbance of one or more of the longer paths, the absorbance of the sample can be calculated.

Samples can also be contained between two thin sheets of optically transparent material like Teflon™ or polyethylene films, rather than having the sample contact the anvil surfaces. As shown in FIG. 9-12, the same sort of column may drawn between the two parts of the sample apparatus as can be drawn between the two thin optical sheets, especially when the anvils of the apparatus are wetted to the film surfaces to minimize reflection at the interface and aid in pulling the measurement column. This would be of significant use where samples are corrosive or dangerous to handle for safety reasons and containment of the sample is preferred. The two containing sheets allow the two parts of the sample apparatus to draw the sample into a column. Differential measurement of the sort discussed above would be of significant value in this sort of measurement as the effects of the interfaces could be minimized with differential measurement. The two sheets can take the form of a small vessel (e.g., see FIG. 9) with flexible walls such that the sample contained can be pulled into a measurement column. The column is pulled by pushing the anvils of the apparatus into the film until contact is made by both films, then drawing the measurement column. The compliance of the film will cause it to remain in contact with the anvils. Wetting the anvils before making contact will assist in maintaining contact and in minimizing reflection at the interface between the film and the optical fiber imbedded in the anvil. Once the measurement column is pulled, absorbance can be measured as a difference in absorbance between two path lengths.

The invention additionally provides systems comprising any of the devices discussed above. Such devices for measuring optical properties (absorption, emission, scattering of light) of samples can be compatible with and/or integrated with other devices such as sample handling systems, sample transfer systems, detectors, processors, microprocessors and the like. Additionally, the invention provides computer program products comprising computer readable medium comprising programs or instructions for implementing and/or integrating various system functions.

The invention also provides methods for detecting and/or quantitating an optical property of a sample. In one aspect, the concentration of an component in a sample can be determined by comparing light transmission by a sample without the component to the sample with the component. The difference in transmitted light intensity can be used to characterize the sample according to:

$$A = -\log(I/I_0)$$

where $I_0$ is level of transmitted light with the component being analyzed absent, and I is the level of light transmitted through the sample in question and A is the absorbance value which can be related to the concentration of the component being analyzed by Beer's law which states that for solutions 1 and 2:

(Absorbance 1)/(Absorbance 2)=(Concentration 1)/(Concentration 2)

Thus, when compared with a known sample, the concentration can be directly determined from the absorbance A.

EXAMPLE

The following example is provided to illustrate certain aspects of the invention, and are not intended to limit the scope of the invention.

Example 1

In order to explore the degree to which the divergent beam optics limited the use of a photometer design's in which the ends of the fiber were significantly separated, an experiment was conducted in which a broadband light source was coupled into a 200-micrometer-diameter multi-mode optical fiber; i.e. the source-side fiber. At the output of this fiber, it was observed that the light diverges. A second multi-mode optical fiber—the detection-side fiber—was placed a distance L from the source-side fiber and positioned so as to share the same centerline as the source-side fiber. Two detection-side fibers were tested: one with 200-micrometer core diameter and the other with 600-micrometer core diameter. A Silicon-photo-diode (Si-PD) at the output end of the detection-side fiber measured the spectrally integrated optical power coupled into the detection-side fiber.

Experimental data collected show that the optical power of the light beam dropped off quickly as fiber-to-fiber distance increased, and the fiber-to-fiber distance that leads to a 90% reduction in transmitted optical power is one centimeter or less, even with a detection-side fiber that has a core diameter that is three times the diameter of the source-side fiber. Thus, it is generally not practical to operate a divergent beam photometer unless the distance between the fiber ends is significantly less than one centimeter.

One of the ways that the present invention seeks to address the problem of short fiber-to-fiber distance is to form a substantially collimated light beam from the output of the source fiber, pass the substantially collimated light beam through the sample, and then focus the substantially collimated light beam into the end of the detector fiber. Because the collimated beam is not divergent, a substantial part of the photo intensity of the source light beam, except, of course, the intensity absorbed by the sample, will be effectively conveyed to the detector, even if the end of the source fiber in the end of the detector fiber are significantly separated.

The present invention utilizes micro-optic-sized beams and collimation optics to solve the problems of divergent photometer beams. Using free-space beam propagation, it is possible to propagate optical beams with diameter 1 mm or less, over several centimeters. An optical beam with diameter $w_0$ and wavelength $\lambda$, and propagating in a material with index of refraction n will remain approximately collimated over the so-called Rayleigh range $z_0$ according to the relationship:

$$z_0 = (\pi \times n \times w_0)/\lambda.$$

Considering beam propagation in air, where n=1, the Rayleigh range reaches from one cm to 100 cm, for beams that range in diameter from 50 to 200 micrometers, and with wavelength $\lambda$=200-800 nm (the ultraviolet and visible range). This shows the feasibility of realizing a sub-millimeter sized optical beam that can travel through micro-liter-volume samples and remain substantially collimated so that the beam can also be efficiently coupled into the end of a detector optical fiber and guided to appropriate detection optics.

Experimental verification was obtained using an experiment in which one ball lens was used to collimate light from the source-side fiber to a diameter of 1 mm or less and a second ball lens was used to couple light back into a multi-mode fiber.

Using source- and detection-side fibers with 200-micrometer core diameter and two 5 mm diameter fused silica ball lenses, more than 55% of the optical power emanating from the source-side fiber was detected at a silicon photo detector (Si-PD) when the ball lenses were separated by L=32 mm or 3.2 cm. In another configuration with a 400-micrometer diameter detection-side fiber, more than 10% of the optical power from the source-side fiber was detected by the Si-PD when L=83 mm or 8.3 cm. In both cases, the collimated optical beams had a minimum diameter of approximately 1 mm.

Thus, it is evident that the use of a collimated light beam in a photometer provides far better coupling efficiency than is available in a divergent beam device, and is effective even over fiber-to-fiber distances of several centimeters. This enables the following advantages:

All optical fibers may be separated from the sample area, and hidden and protected from breakage or bending during use of the spectrophotometer, leading to less variability and smaller systematic errors associated with variable fiber transmission.

Greater flexibility in designing the sample zone. For example, a microvolume cuvette could readily be inserted in the collimated portion of the beam.

Greater flexibility in designing the light path. For example, the collimated light path can be diverted 90 degrees by passing the light through a right angle beam-steering prism. In this way, the height requirement above the sample can be significantly reduced over a fiber that must be looped over (no sharp bends) into a vertical position over the sample.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A device for directing light to and from a liquid sample within a sample containment area, comprising:
   a light source for providing light to the liquid sample;
   a collimating element for collimating light from the light source and for providing substantially collimated light to the sample;
   a first light path-defining element for directing light from the light source to the collimating element;
   a second light-path defining element for receiving light from the sample; and
   a steering prism for receiving substantially collimated light from the collimating element and directing the light to the sample.

2. The device of claim 1, wherein the substantially collimated light beam is about 1 mm or less.

3. The device of claim 1, wherein the sample containment area comprises about 1 cm or greater.

4. The device of claim 1, wherein the first light path-defining element comprises an output end for directing light to the collimating element and wherein the second light path-defining element comprises an input end for receiving light from the sample and wherein neither the output end of the first light-path defining element nor the input end of the second-light path defining element forms any portion of the sample containment area.

5. The device of claim 1, wherein the sample containment area comprises two surfaces that are substantially parallel during operation of the device.

6. The device of claim 1, wherein the steering prism forms at least a portion of the sample containment area.

7. The device of claim 1, further comprising a light-focusing element for directing a focused light beam to an input end of the second-light path defining element.

8. The device of claim 7, wherein the light-focusing element forms at least a portion of the sample containment area.

9. The device of claim 1, wherein the device comprises a plurality of steering prisms.

10. The device of claim 1, wherein the steering prism comprises a right angle beam steering prism.

11. The device of claim 1, wherein the sample containment area is configured to receive a sample container comprising about 1 cm path length.

12. The device of claim 1, wherein the sample containment area receives a sample comprising 0.1-5 µl.

13. The device of claim 12, wherein the sample containment area receives a sample comprising less than about 2 µl.

14. The device of claim 1, wherein the collimating element comprises a ball lens.

15. The device of claim 1, the substantially collimated optical beam comprises a diameter less than about 1 mm over a distance which corresponds to a distance that is greater to or equal than at least one dimension of the sample containment area.

16. The device of claim 1, wherein the first and/or second light-path defining elements comprise an optical fiber.

17. The device of claim 1, wherein the second light path-defining element is coupled to or is couplable to a photodetector.

18. The device of claim 1, wherein the second light path-defining element is coupled to a spectrometer.

19. The device of claim 1, wherein the second light path-defining element is coupled to a spectrometer with a one-dimensional photo-diode array as the photodetector.

20. The device of claim 16, wherein the first and/or second light-path defining elements are immovable during operation of the device.

21. The device of claim 1, wherein the steering prism comprises a Porro prism.

22. The device of claim 5, wherein a sample is held by surface tension between the two substantially parallel surfaces during operation of the device.

23. The device of claim 5, wherein the device further comprises a spacing controller that varies the distance between the surfaces.

24. The device of claim 5, wherein the device further comprises a mechanism for monitoring the distance between the surfaces.

25. The device of claim 1, wherein the sample containment area is configured to receive a container comprising a passageway for holding a sample in the passageway via surface tension between the sample and walls defining the passageway.

26. The device of claim 23, wherein the container comprises a capillary channel.

27. The device of claim 23, wherein the container is removable from the device.

28. The device of claim 1, wherein the device further comprises a removable container within the sample containment area.

29. The device of claim 8, wherein the container comprises an at least partially transparent capillary.

30. The device of claim 28, wherein the container comprises a square cross-section through at least a portion of the container.

31. The device of claim 26, wherein the container comprises a rectangular cross-section through at least a portion of the container.

32. The device of claim 5, wherein at least one of the surfaces is at least partially transparent.

33. The device of claim 32, wherein both of the surfaces are at least partially transparent.

34. A system comprising a device of claim 1 and a detector, wherein the detector is in optical communication with the second light path-defining element.

35. The system of claim 34 further comprising a read-out device for providing data relating to an optical property of the sample.

36. The system of claim 34, further comprising a user interface for receiving inputs from a user relating to operation of the device.

37. The system of claim 34, further comprising a processor for controlling a function of the system.

38. The system of claim 34, wherein the processor compares an optical property of the sample to an optical property of a reference standard.

39. A method comprising:
placing a liquid sample in a sample containment area of the device of claim 1;
determining an optical property of the sample; and
utilizing the optical property to determine component concentration in the sample.

40. The method of claim 39, wherein the method comprises placing a sample in a sample container prior to placing it in the sample containment area.

41. The method of claim 39, wherein the sample comprises less than about 5 µl.

42. The method of claim 39, wherein the sample comprises about 2 µl or less.

43. The method of claim 39, wherein the liquid sample comprises a nucleic acid.

44. The method of claim 39, wherein the liquid sample comprises DNA.

45. The method of claim 39, wherein the liquid sample comprises RNA.

46. The method of claim 39, wherein the liquid sample comprises a protein, polypeptide or peptide.

47. The method of claim 39, wherein the method further comprises correlating an optical property of the sample to a concentration of a biomolecule in the sample.

48. The method of claim 39, wherein the optical property is determined at a plurality of different wavelengths of light.

* * * * *